(12) United States Patent
Gitman et al.

(10) Patent No.: US 10,285,729 B2
(45) Date of Patent: May 14, 2019

(54) FINGER-HELD INSTRUMENT ADAPTED FOR SUPPORTING OR SHIELDING A USER'S FINGER

(71) Applicant: SCALPAL LLC, Wilmington, DE (US)

(72) Inventors: Eliot Robert Gitman, Jerusalem (IL); Tuvia Gitman, Jerusalem (IL)

(73) Assignee: SCALPAL LLC, Wilmington, DE (US)

(*) Notice: Subject to any disclaimer, the term of this patent is extended or adjusted under 35 U.S.C. 154(b) by 371 days.

(21) Appl. No.: 14/758,293

(22) PCT Filed: Sep. 30, 2013

(86) PCT No.: PCT/IL2013/050807
§ 371 (c)(1),
(2) Date: Jun. 29, 2015

(87) PCT Pub. No.: WO2014/102764
PCT Pub. Date: Jul. 3, 2014

(65) Prior Publication Data
US 2015/0351787 A1    Dec. 10, 2015

(30) Foreign Application Priority Data
Dec. 31, 2012   (IL) .......................................... 224082

(51) Int. Cl.
| A61B 17/3211 | (2006.01) |
| B25G 1/10 | (2006.01) |
| A61B 17/3213 | (2006.01) |
| A61B 17/00 | (2006.01) |
| A61B 90/00 | (2016.01) |

(52) U.S. Cl.
CPC ...... *A61B 17/3211* (2013.01); *A61B 17/3213* (2013.01); *B25G 1/102* (2013.01); *A61B 2017/00424* (2013.01); *A61B 2017/32113* (2013.01); *A61B 2090/036* (2016.02); *A61B 2090/0801* (2016.02)

(58) Field of Classification Search
CPC ............ A61B 17/3211; A61B 17/3213; A61B 2017/32113
See application file for complete search history.

(56) References Cited

U.S. PATENT DOCUMENTS

| 2,215,125 A | 9/1940 | Maltz |
| 3,974,833 A | 8/1976 | Durden, III |
(Continued)

FOREIGN PATENT DOCUMENTS

| DE | 20209870 U1 | 10/2003 |
| FR | 1094820 A | 5/1955 |
(Continued)

*Primary Examiner* — Shaun David
(74) *Attorney, Agent, or Firm* — Smith, Gambrell & Russell, LLP

(57) ABSTRACT

A finger-held instrument (25) having a handle (10) supporting a working tip (11, 31) on a mount (15) located at an end of the handle that is held proximate a working surface (43) during use, said handle being characterized by a projection (20) supported by or on said portion proximate the working tip and being dimensioned and shaped for supporting or shielding a user's finger (26a, 27a, 29a) and for exerting a contact force on the working surface so as to allow fine control of the working tip during use.

25 Claims, 16 Drawing Sheets

(56) References Cited

U.S. PATENT DOCUMENTS

| | | | |
|---|---|---|---|
| 4,173,071 A * | 11/1979 | Ishida | A61B 17/3213 30/339 |
| 5,026,385 A | 6/1991 | Schutte et al. | |
| 5,341,822 A | 8/1994 | Farr et al. | |
| 5,601,584 A | 2/1997 | Obagi et al. | |
| 8,745,825 B2 | 6/2014 | Gitman et al. | |
| 8,850,662 B2 | 10/2014 | Gitman et al. | |
| 9,717,521 B2 | 8/2017 | Gitman | |
| 2008/0077146 A1 | 3/2008 | Pernsteiner et al. | |
| 2010/0005630 A1* | 1/2010 | Gitman | A61B 17/3213 16/430 |
| 2015/0148596 A1 | 5/2015 | Gitman | |
| 2017/0135716 A1 | 5/2017 | Endo | |

FOREIGN PATENT DOCUMENTS

| | | |
|---|---|---|
| GB | 2271738 A | 4/1994 |
| WO | 0249520 A1 | 6/2002 |
| WO | 2004002335 A1 | 1/2004 |
| WO | 2010004541 A1 | 1/2010 |

\* cited by examiner

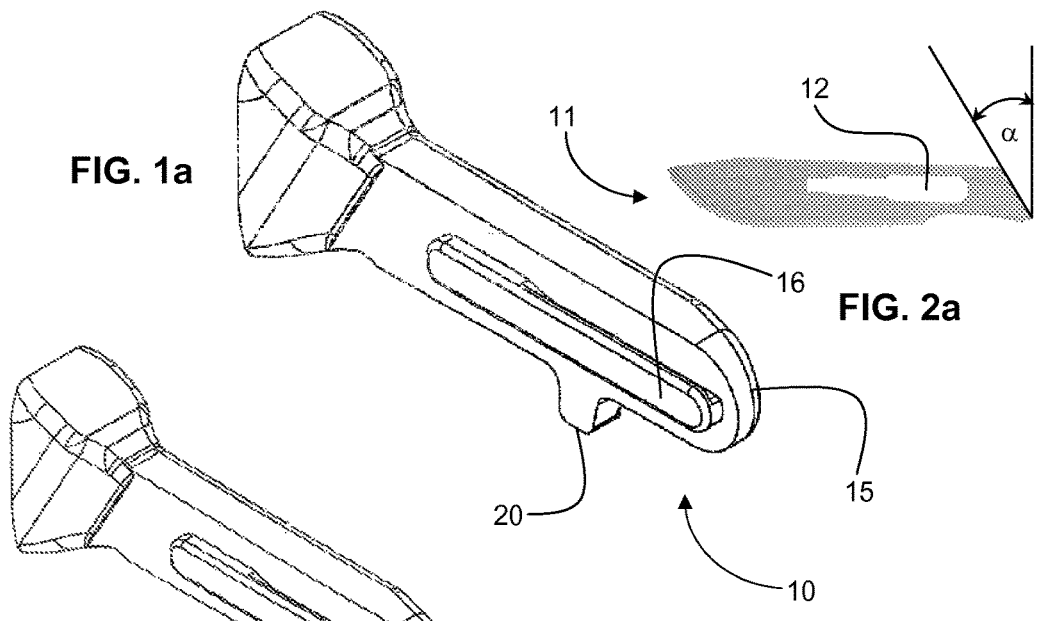
FIG. 1a
FIG. 2a
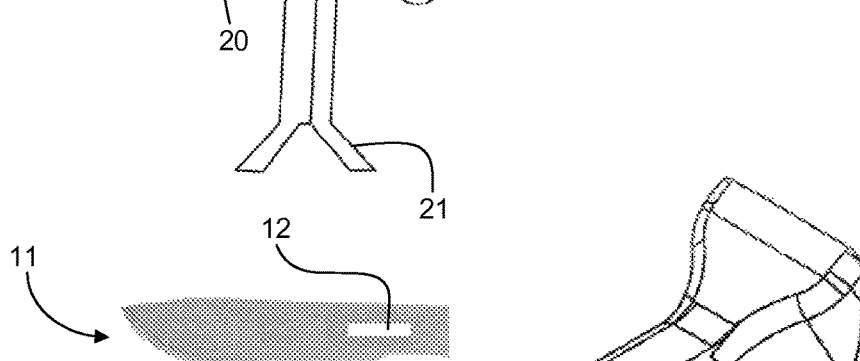
FIG. 1b
FIG. 2b
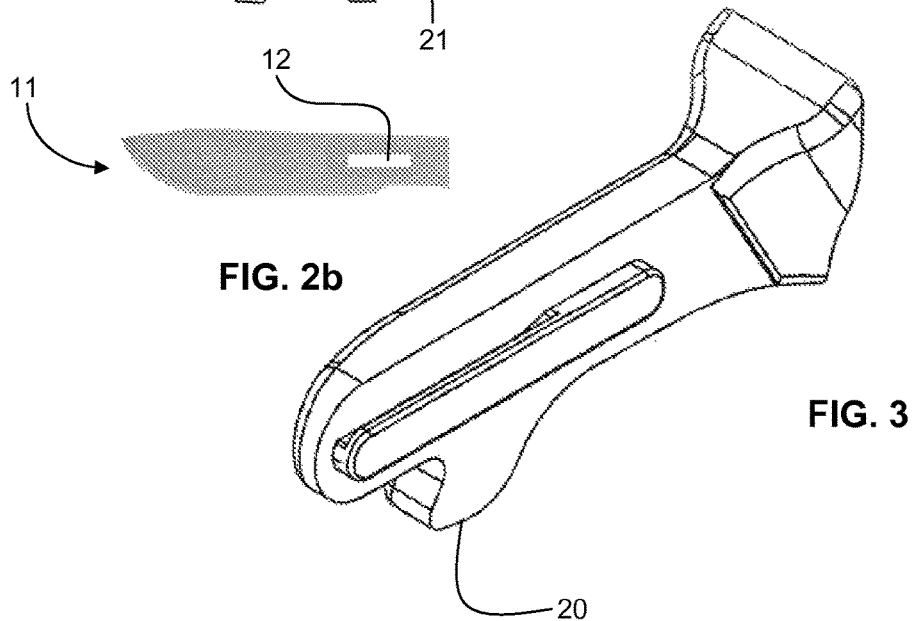
FIG. 3

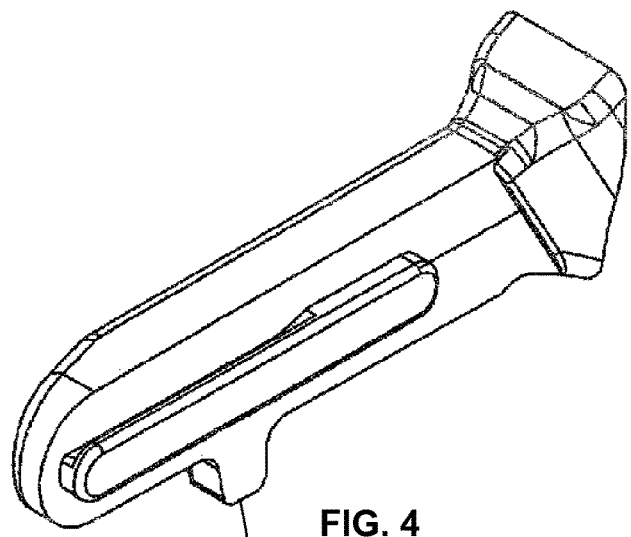
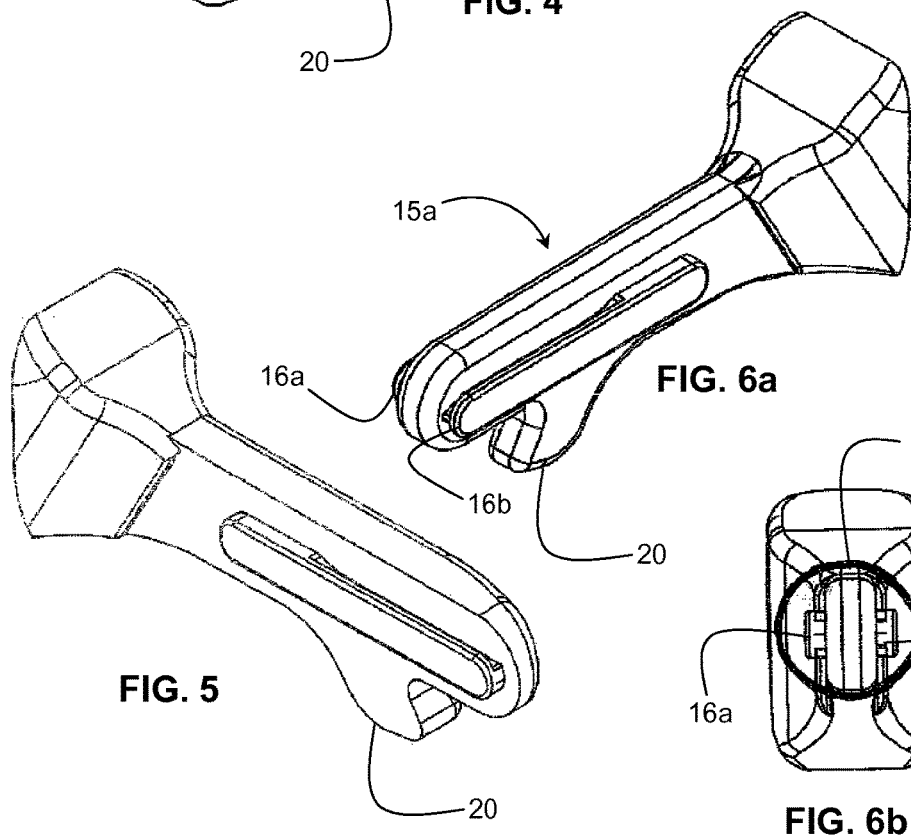

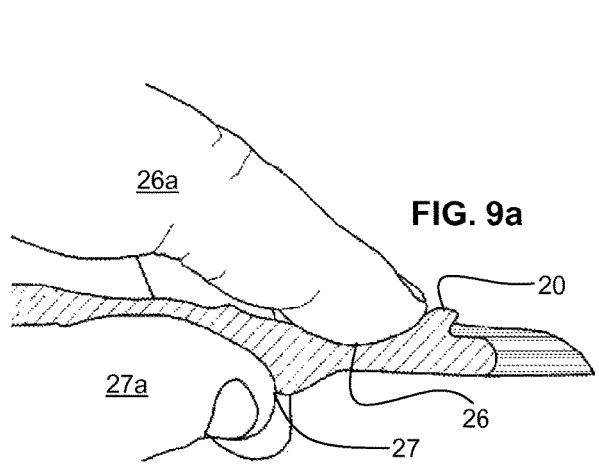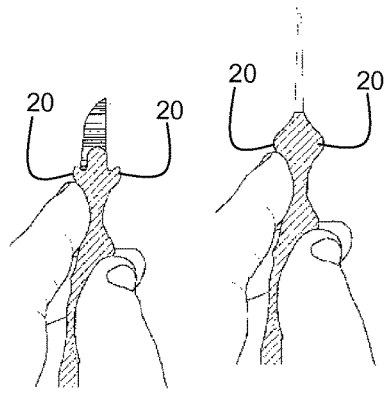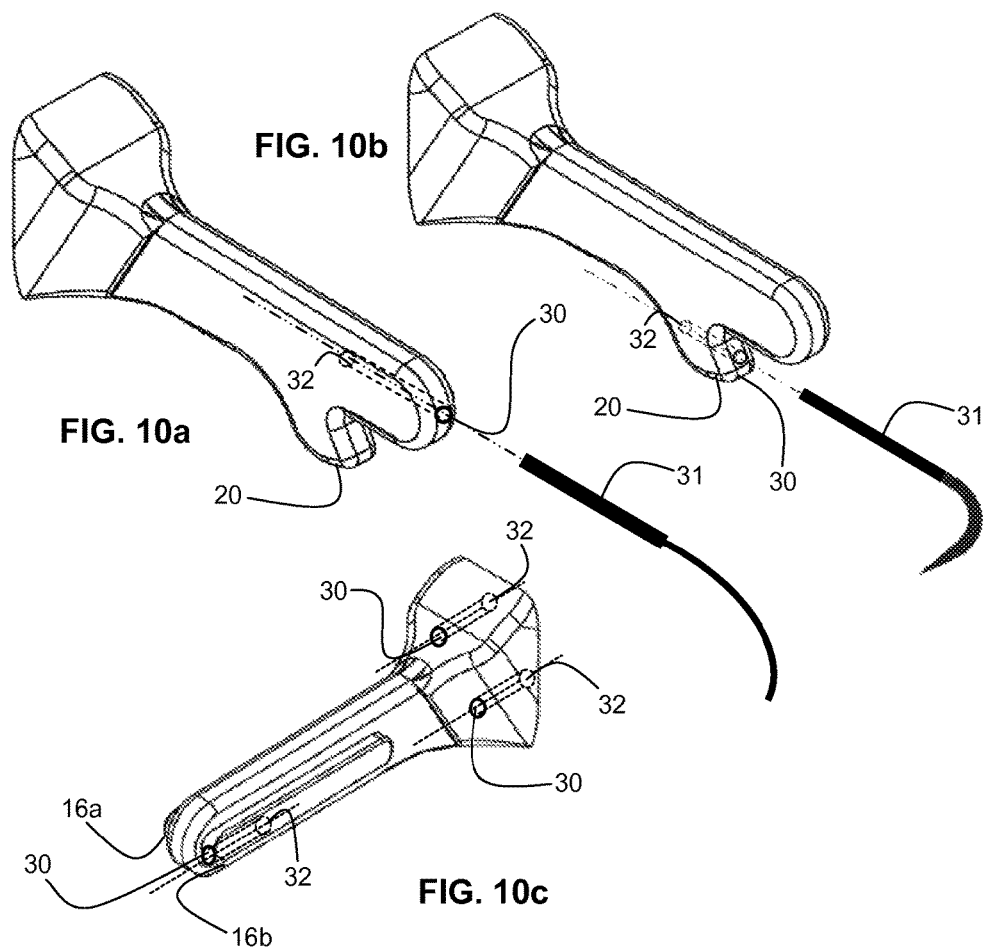

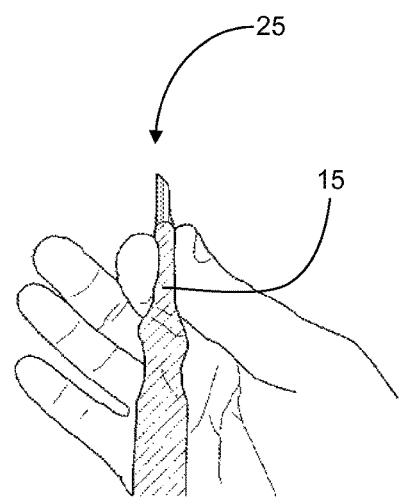
FIG. 11
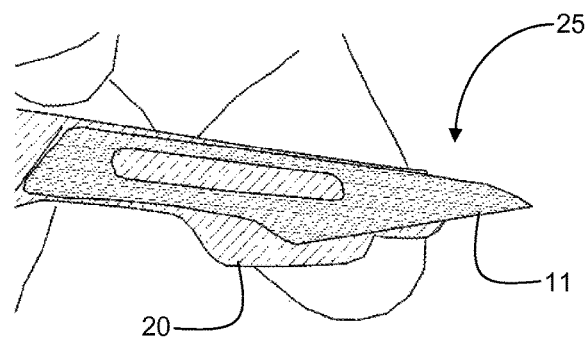
FIG. 12
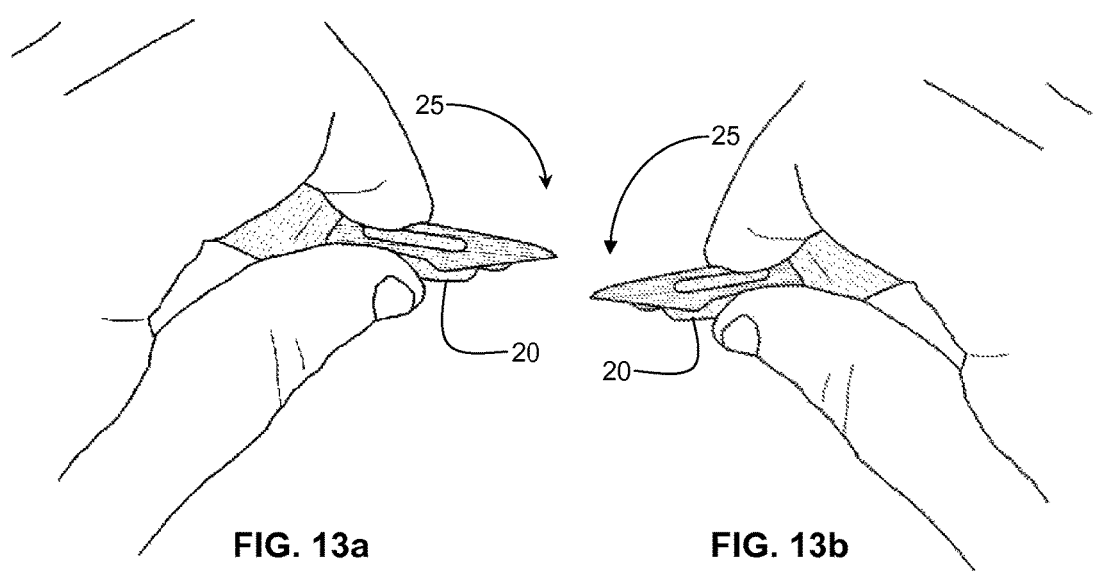
FIG. 13a  FIG. 13b

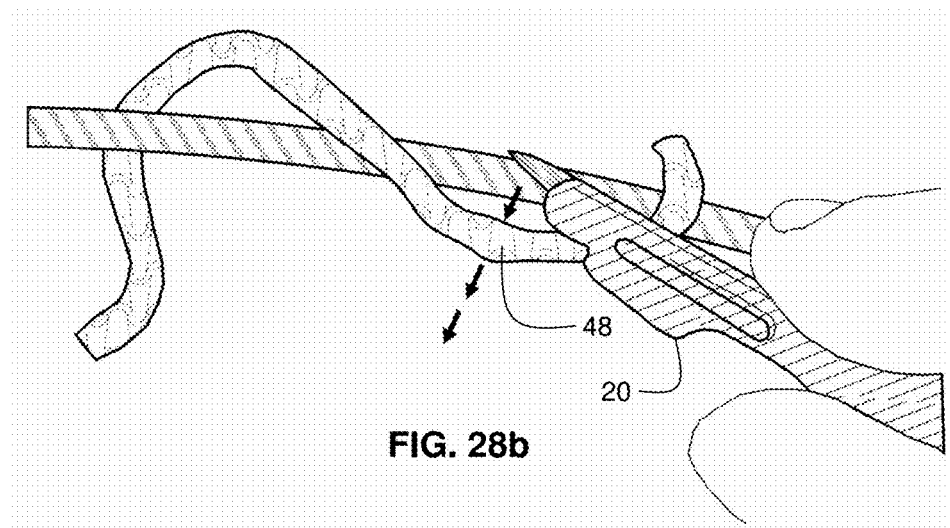
FIG. 28b
FIG. 29b
FIG. 29a
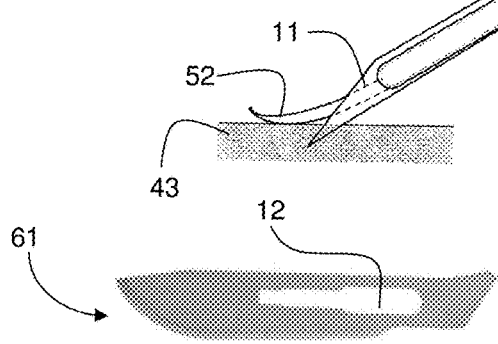
FIG. 30b
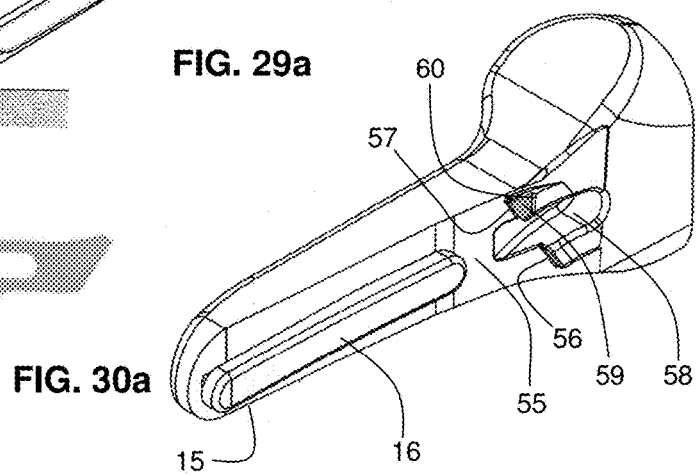
FIG. 30a

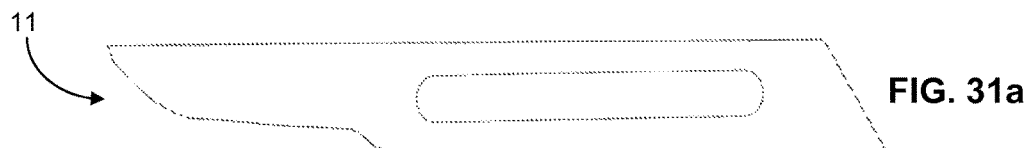
FIG. 31a
FIG. 31b
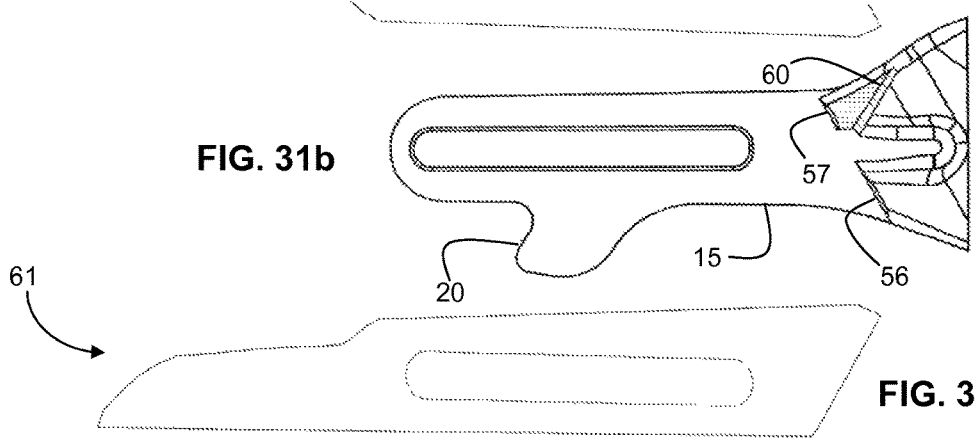
FIG. 31c
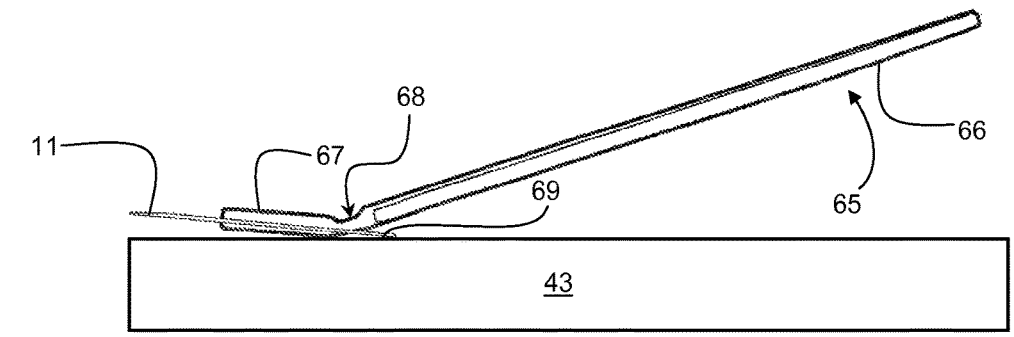
FIG. 32a
(Prior art)
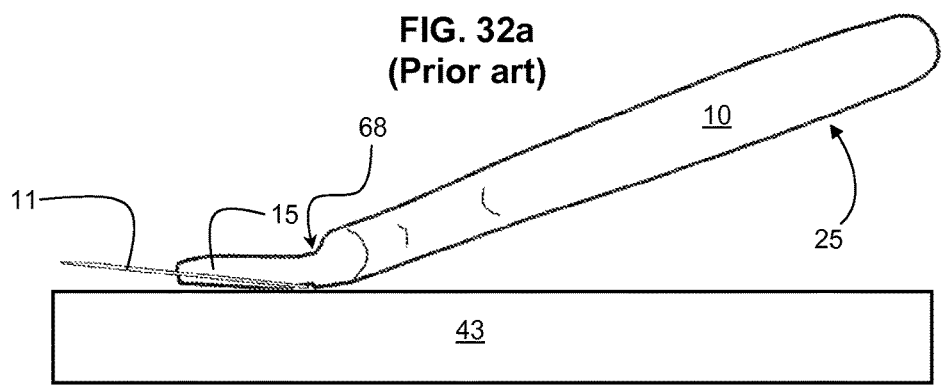
FIG. 32b

FINGER-HELD INSTRUMENT ADAPTED FOR SUPPORTING OR SHIELDING A USER'S FINGER

FIELD OF THE INVENTION

This invention relates to finger-held instruments, particularly but not only surgical scalpels.

BACKGROUND OF THE INVENTION

Surgical scalpels are finger-held in a manner similar to a marking instrument and must be comfortable for the surgeon or craftsman as well as being amenable to fine control. To this extent, it is important that they can be held easily and that they allow the surgeon or other artisan to control the depth and extent of cut both into and along the skin. Scalpels are known having a retractable or non-retractable blade and a depth gauge that adjusts the extent to which the blade protrudes from a body portion. However, the present invention relates principally to a surgical scalpel comprising a reusable handle having a tang at one end on which a replaceable slotted blade is mounted. The blade is discarded after use while the handle may be either disposable or intended for repeated use.

Hand held instruments such as scalpels and writing instruments typically have an elongated handle supporting at a tip a working portion that may be, for example, a pencil lead, nib or blade. The handle is held near the end between the thumb and middle finger, which acts as a fulcrum about which the instrument may be tilted under control of the index finger, which is held forward of the thumb and middle finger close to the tip so as to allow very fine adjustment.

U.S. Pat. No. 6,793,427 discloses a writing instrument having near its tip an upwardly protruding shaped projection that may serve as a ledge for supporting the index finger.

When performing delicate operations such as cutting, particularly but not only during surgery, very fine control is needed. This is best achieved by holding the instrument as close as possible to the working tip. For example, during surgery better control of a knife or scalpel is achieved by holding the scalpel close to the blade. Often scalpels have a blade attached either fixedly or removably to an elongated handle: it is obvious that it is difficult to control such an instrument if it is gripped remote from the blade just as a pen or pencil cannot be used in a controlled manner if gripped remote from the nib or lead. However, while there is no risk of injury to the user who grips a pen or pencil close to the nib or lead, this is not at all the case with a knife or scalpel having a sharp blade since if the user's finger inadvertently brushes against the blade, there is a significant risk, and even likelihood, of being cut. Not only is this unpleasant for the surgeon, but the possible contamination of the patient by the surgeon's blood is a very severe health hazard to the patient himself.

This risk imposes a limit to the proximity to the blade with which known knives and surgical scalpels may safely be held. Commonly, the handle is shaped for gripping so that the user's fingers are kept well clear of the blade. However, for the reasons stated above this militates against the very fine control of the blade that may be required during surgical operations or delicate craftsmanship, such as paper-cutting and the like.

Cutting operations are not always normal i.e. at an angle of 90° to the surface of a workpiece and it may be necessary to rotate the edge of the blade so as to insert the blade at an angle to the working surface, for example, when cutting a beveled edge. Some knives such as those used for paper cutting, may be equipped with a rotatable tip or tang to which the blade is fixed. However, also in surgical scalpels, there may be a need to insert the blade at an angle to the skin surface and this is difficult to achieve without applying finger pressure against a side surface of the blade, with the attendant risk of injury.

Often accurate cutting of thin sheet material, be it paper, plastic sheeting, skin and the like requires that the material be kept taut during the cutting. Otherwise, there is a risk that the material may buckle or fold, militating against or preventing a straight and accurate cut. Commonly, this requirement is met in practice by the user securing a remote edge of the material with an instrument or with the fingers of the weak hand (i.e. the hand not holding the knife) and exerting a slight pulling force to stretch the material against the direction of the cut, while drawing the blade in the opposite direction with the other hand.

In all these cases, accurate control of the instrument is achieved by manipulating the working tip of the instrument using finger pressure: and this is impractical in known designs of knives owing to the risk of injury.

It has been found that mass of the tool is also an important factor in determining comfort. A typical prior art disposable non-retractable scalpel is formed of plastics and weighs approximately 4 gram. This is very light but susceptible to fracture where the blade is affixed to the tang owing to the very narrow cross-section of the tang. A typical prior art non-disposable and non-retractable scalpel is formed of stainless steel weighing approximately 22 gram or titanium weighing approximately 14 gram, but which is prohibitively expensive. This is much stronger such that the handle is not amenable to fracture during use. However, whereas plastic is resilient and gives slightly when pressure is applied, metal handles are much more rigid and intolerant. Consequently, excessive pressure is applied directly to the blade, which is liable to snap. Furthermore, its weight tends to induce an imbalance when the scalpel is rotated during use since there comes a point where the center of gravity of the knife shifts and causes the scalpel to flip over.

FIGS. 34a to 34c show pictorially different views of a prior art surgical scalpel 80 as disclosed in U.S. Design Pat. No. 589,619 to Wu. The scalpel 80 includes a mount 81 supporting a slotted blade 82 mounted on a flat side surface of the mount and having a shield portion 83 that projects outwardly from a side surface of the mount so as to be perpendicular to the surface of the blade and thus parallel to a workpiece 84. During use, as seen in FIGS. 34b and 34c, the shield portion 83 forms a ledge against which the surgeon's finger rests but owing to the fact that the shield portion 83 projects outwardly in a plane that is orthogonal to the blade 82, it lies transverse to the workpiece 84, which is therefore incapable of exerting a contact force on the shield portion 83. Thus the shield portion 83 serves to protect the surgeon's finger 85, but it does this while maintaining both the shield portion 83 and the finger 85 remote from the workpiece and thereby militates against the very fine control that requires stable support of the scalpel during use.

U.S. Pat. No. 3,974,833 discloses a disposable electro-surgical cauterizer having an elongated hollow metal electrode and suction tube encased in a plastic contoured handle having ridges near the tip of the cauterizer.

DE 202 09 870 discloses a knife with a planar mount having a protrusion that is accommodated within a slot of a blade. A shield slides on the mount and can be moved forward to a position where the blade is concealed and backward to a working position where the blade projects through a slot in the projection. The shield supports a projection which could shield a user's finger.

WO 2004/002335 discloses a scalpel having a blade fixed to an arc-shaped bearing surface provided on the front end of the scalpel handle.

WO 2002/049520 discloses a scalpel handle comprising a first upper curved body anatomically corresponding to the curved direction of the forefinger, and a second underlying body prolonging the first one, having an asymmetrical overturned-saddle shape.

U.S. Pat. No. 5,601,584 discloses a scalpel having an elongated handle from one end of which a cutting blade extends laterally, and a depth-of-cut limiting plate extending laterally from the same end and disposed parallel to and spaced apart from the cutting blade.

US 2008/077146 discloses a surgical tool for cutting the annulus of a spinal disc having a stop surface configured to contact the annulus during cutting to prevent further longitudinal movement of the surgical blade into the annulus, thus limiting the size of the incision.

GB 2 271 738 discloses a releasable grip for a surgical knife having a profiled, releasable gripping portion allowing the thumb, index finger and middle finger to be positioned comfortably and accurately enabling controllable and accurate incisions to be made up to the maximum depths of the usable part of the blade.

SUMMARY OF THE INVENTION

It is therefore an object of the invention to provide a finger-held instrument having a handle supporting a working tip, where the handle is adapted so as to facilitate safe manipulation of the working tip of the instrument using finger pressure.

This object is realized in accordance with the invention by a finger-held instrument having a handle supporting a working tip on a mount and having the features of the respective independent claims.

In one aspect, the present invention is directed to a finger-held instrument having a handle supporting a working tip on a mount located at an end of the handle that is held proximate a working surface during use, said handle being characterized by a projection supported by said portion proximate the working tip and being dimensioned and shaped for supporting or shielding a user's finger and for exerting a contact force on the working surface so as to allow fine control of the working tip during use.

In accordance with another aspect of the invention, a method for using the hand-held instrument includes:

holding the handle near the working tip between the thumb and middle finger, using the index finger to apply a pulling or pushing force to the working tip against a workpiece, and maintaining the projection in sliding contact with the workpiece.

In accordance with an embodiment of the invention, the hand-held instrument is a surgical scalpel for use during a therapeutic or diagnostic procedure.

Within the context of the present invention and claims, it is to be understood that the term "projection" relates to an element that projects from the tang or mount to which the working tip is fixed and extends.

In some embodiments, the instrument is a knife in which case the working tip is a blade of the knife and the projection extends beneath a cutting edge of the blade.

In some embodiments the mount and the projection are non-textured in order to facilitate rotation of the hand-held instrument. In other embodiments they may be textured to improve gripping.

In some embodiments the handle and the portion thereof to which the working tip is attached form a continuous contoured surface so that the instrument can be moved against a working surface without the handle snagging the working surface.

A precision instrument having this feature is preferably contoured close to the working tip to allow the surgeon to support the instrument between a thumb and finger with the working tip against the working surface and to rotate the instrument relative to the working surface in any direction in a finely controlled manner. This is particularly useful for a knife such as a surgical scalpel and for other surgical instruments such as electrodes used for cauterization during surgery, as well as probes and so on. The contoured surface of the handle also provides a reduced profile that permits the user looking down the length of the instrument toward the working tip to see more easily the point of contact between the working tip and the working surface. This also facilitates better control and renders the tool more precise. Furthermore, since the contoured surface of the handle is located in a defined orientation relative to the working tip, the contoured surface also provides tactile feedback of the location and orientation of the working tip, even without the user needing actually to see the working tip.

Furthermore, the blade may be mounted substantially flush on the handle thus allowing the user to hold the blade substantially flat against the working surface. In the case of a surgical scalpel, the surgeon can then use the blade to slice artifacts that erupt from a surface of the skin such as common plastic surgical applications. Additionally, the projection allows the blade to be maintained in spaced-apart relationship with the working surface so that it can effectively hover above the working surface at a fixed distance. This is very difficult to achieve in known scalpels.

In such case, the handle may be contoured to allow the finger to act as a depth gauge so that the blade can slice without being supported on the working surface. This permits the user to remove fractional slices of a protruding artifact.

A scalpel according to the invention has a handle of significantly larger cross-section than typical plastic scalpels, such that it is less prone to fracture. Nevertheless it is formed of plastics having an overall mass in the region of 14 gram, which is heavier than known plastic scalpels but substantially lighter than those formed of metal. Yet though heavier, being formed of plastic, it is not completely rigid and yields slightly to excess pressure without fracturing the blade.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1a is a pictorial representation showing a detail of a handle of a surgical scalpel having a projection dimensioned to provide sliding contact with a surface of a patient's skin during use;

FIG. 1b shows a further modification of the instrument allowing for stable elevation of the tool above a workpiece;

FIGS. 2a and 2b show different blades for use with such a handle;

FIGS. 3 to 6a and 6b are pictorial representations showing details of a working end of a handle according to different embodiments of the invention;

FIGS. 7 to 9c are pictorial representations showing how the projection serves as a finger abutment during use;

FIGS. 10a to 10h show modifications of the instrument allowing for coupling of external accessories thereto;

FIG. 11 shows pictorially an instrument according to the invention having a recessed narrow-waist working tip for easy gripping;

FIGS. 12 to 15 are pictorial representations showing use of the surgical scalpel;

FIGS. 28a and 28b show use of the projection for dislodging material and preventing inadvertent damage thereto during a cutting action;

FIGS. 29a and 29b show respectively an instrument and a tool guide or gauge according to another embodiment of the invention;

FIGS. 30a and 31b show alternative mounts configured for supporting either a blade having a slanted rear edge as shown in FIG. 2a or a blade of opposite orientation as shown in FIG. 30b;

FIGS. 31a and 31c show respectively elevations of blades having mutually opposed slanting rear edges;

FIG. 32a shows pictorially a prior art surgical scalpel whose handle is bent at a fixed angle close to the mount;

FIG. 32b shows pictorially a surgical scalpel according to the invention whose handle is formed of a material that allows it to be bent at a desired angle where it meets the tang;

DETAILED DESCRIPTION OF EMBODIMENTS

Figure 7:
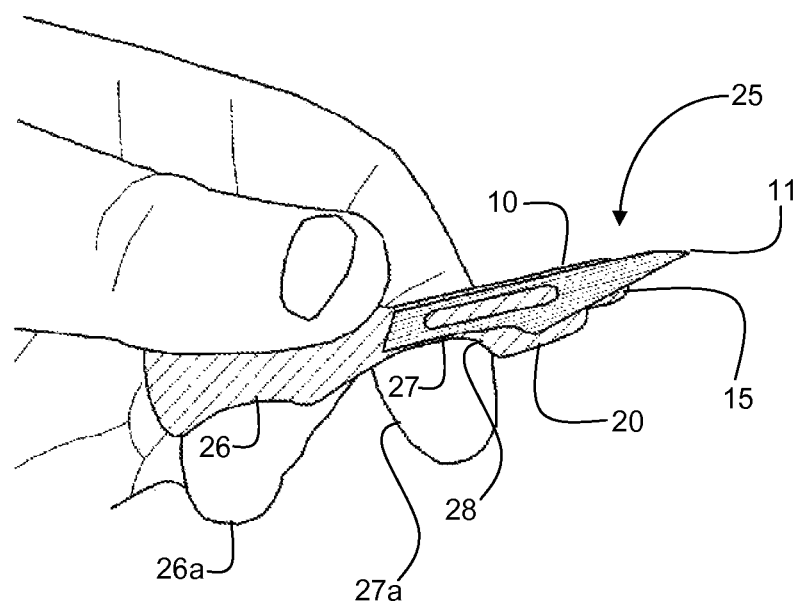

In the following description of some embodiments, identical components that appear in more than one figure or that share similar functionality will be referenced by identical reference symbols.

With reference to FIGS. 1 to 5, there is shown a detail of the tip-end of a handle 10 according to different embodiments of a surgical scalpel (not shown in detail) adapted for receiving a removable blade 11 shown in FIGS. 2a and 2b having an elongate keyhole slot 12. The blade shown in FIG. 2a has a rear edge that is oriented at an acute angle α to the axis of the blade. However, it is to be understood that the design of the blade is not a feature of the present invention and the rear edge may be orthogonal to the longitudinal axis of the blade as shown in FIG. 2b. Likewise, although in conventional scalpels such as shown in FIG. 2a, the blade is slotted and keyed to the tip-end of the handle, it is to be understood that this is not a feature of the invention and other types of blades such as shown in FIG. 2b are equally suitable. The handle 10 has a mount 15 for affixing the blade supporting an elongate protrusion 16 that is complementary to the slot 12 in the blade, which it engages when the blade 11 is mounted on the handle 10. The mount 15, which constitutes a portion of the handle also referred to as a tang, may be narrower than the blade such that part of the blade overhangs the tang and provides purchase for easy removal of the blade 11, which constitutes a working tip. Alternatively, the mount 15 may be dimensioned for supporting the blade 11 with no overhang. In either case, the blade 11 may be either removable so as to allow repeated use of the handle or it may be fixedly attached to a disposable handle. The elongate protrusion 16 is recessed for sliding accommodation of the narrow portion of the keyhole slot 12. These features are not described in further detail since they are known per se for example from U.S. Design Pat. No. 101,325 to Brown. Alternatively, the blade may be adapted for insertion into a slotted bore formed through an end of the mount 15. Such a construction is commonly employed in craft knives and is also known per se.

Figure 34A:
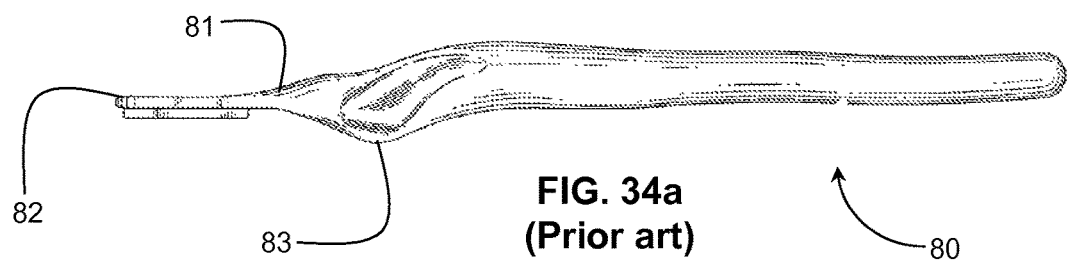
FIGS. 34a to 34c show pictorially different views of a prior art surgical scalpel whose mount includes a shield portion that is incapable of exerting a contact force.
Figure 34B:
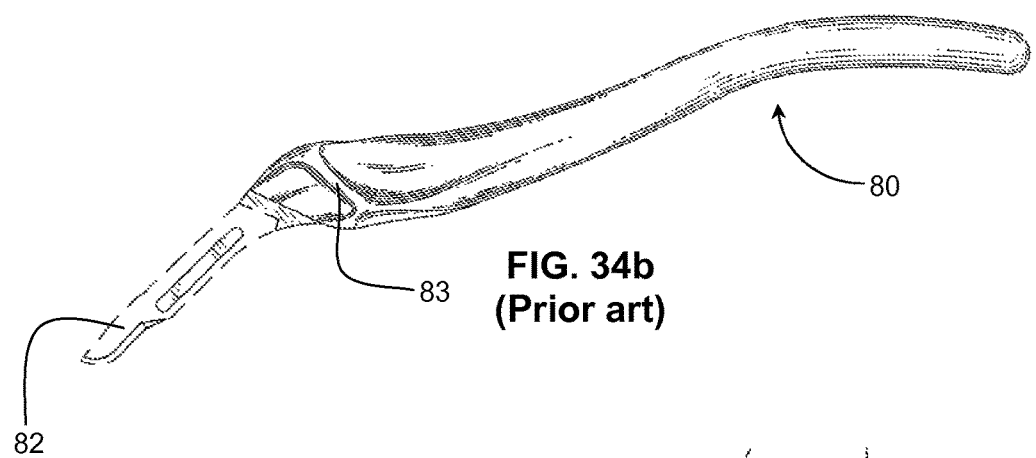
Figure 34C:
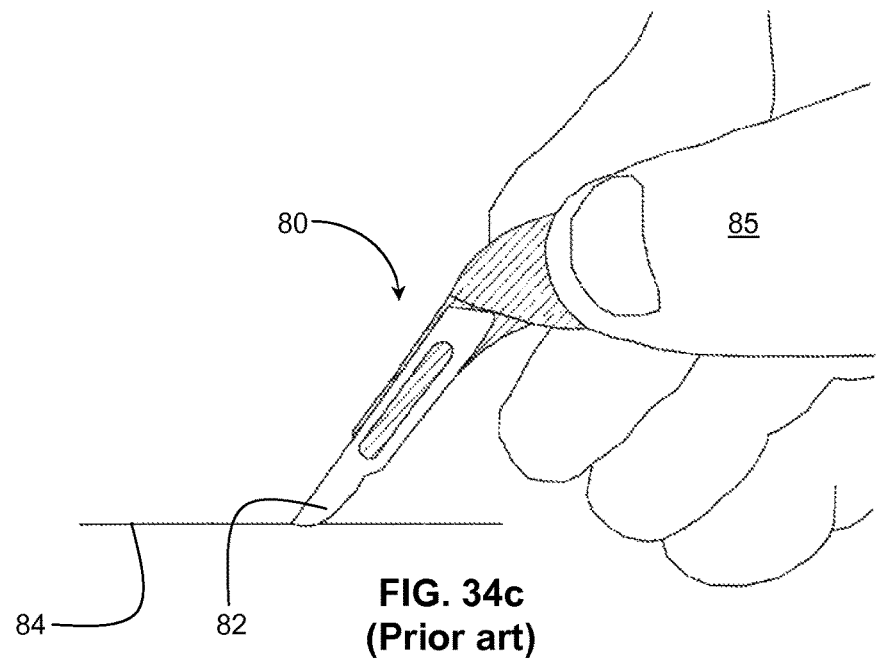

The handle 10 has a projection 20 supported by the mount 15 and being dimensioned to provide sliding or hovering contact with the patient's skin constituting a working surface during use. This allows the projection 20 to exert a contact force on the working surface owing to its being oriented parallel to the blade 11 rather than orthogonal thereto as in the prior art scalpel of U.S. Design Pat. No. 589,619 shown in FIG. 34b. In surgical applications, the working surface i.e. skin is elastic, and the projection 20 may be adapted to stretch the skin as the blade 11 is drawn across the skin during use. The projection 20 also serves as a fulcrum for tilting the blade 11 toward the patient's skin in order to penetrate the flesh. In some embodiments, the projection 20 may be elongated as shown in FIG. 1b and may optionally be provided with a forked support shown pictorially as 21 that may be pivotally supported on a fulcrum. The elongated projection 20 may be a uniform projection or an extension may be releasably attachable to the projection 20. The same principles apply when cutting other types of sheet material such as plastic sheeting or even paper, where an area in the immediate proximity to the blade is maintained taut during cutting. It is thus to be noted that the benefits of the invention are not confined to surgical use and are also applicable to craft knives all of which are thus encompassed by the invention and embraced by the appended claims.

In FIGS. 1 to 5 only the working end of the handle 10 is shown. Commonly, the blade 11 is fixed to one end of an elongated handle, in which case the working end of the handle where it is gripped by the user is shaped as shown in the figures.

However, the invention is not restricted for use with instruments having an elongated handle. FIG. 7 is a pictorial representation of a different embodiment of a surgical scalpel having a short handle showing how the projection serves as a finger abutment during use. The shortness of the handle allows it to be held in the hand with its proximal end supported by the palm. The shield is located at the distal end of the handle so as to support the user's finger very close to the workpiece, thus allowing the user to apply force in the immediate vicinity of the workpiece. This is particularly useful for dental and other surgical applications where fine control is required in a restricted space such as the oral cavity.

FIGS. 6a and 6b show an embodiment of a scalpel 25 whose handle 10 supports a doubled-sided mount 15a and projection 20 as described above. The mount 15a supports on opposite sides thereof a respective elongate protrusion 16a and 16b that are complementary to the slot 12 in the blade, thus allowing either a single blade to be mounted on either side of the handle or for allowing two blades to be mounted on opposite sides of the handle simultaneously. FIG. 6b shows a rotatable collet 17 that allows the working tip to be rotatably attached to the handle.

FIG. 7 shows an embodiment of a scalpel 25 with a short handle 10 having toward its proximal end in a lower surface thereof a first depression 26 shaped for accommodating the user's middle finger 26a. Owing to the fact that the finger is accommodated within the depression, it is difficult to distinguish between the depression and the finger. To this end, the finger will be identified using the same reference as the corresponding depression but with the addition of the symbol "a" even when different fingers are supported by the same depression. The mount 15 is integral with the handle 10 and constitutes a portion of the handle that is held proximate a working surface during use and supports a fixed or removable blade 11 in known manner. A projection 20 is supported by the mount 15 proximate the blade and provides sliding contact with the working surface during use or allows the blade to be held in a spaced apart relationship thereto. The handle 10 has a second depression 27 whose distal end abuts a rear edge 28 of the projection 20, and which is shaped for supporting a user's index finger 27a so as to allow fine control of the blade during use in some uses of the scalpel, the rear edge 28 may serve as an abutment against which the user's index finger rests and which may serve to allow pressure to be applied by the index finger in order to edge the blade 11 forward by a small, finely controlled distance. In this embodiment, the user's thumb rests against the upper edge of the handle, allowing the instrument to be tilted sideways by slight sideways rotation of the thumb.

Figure 8:
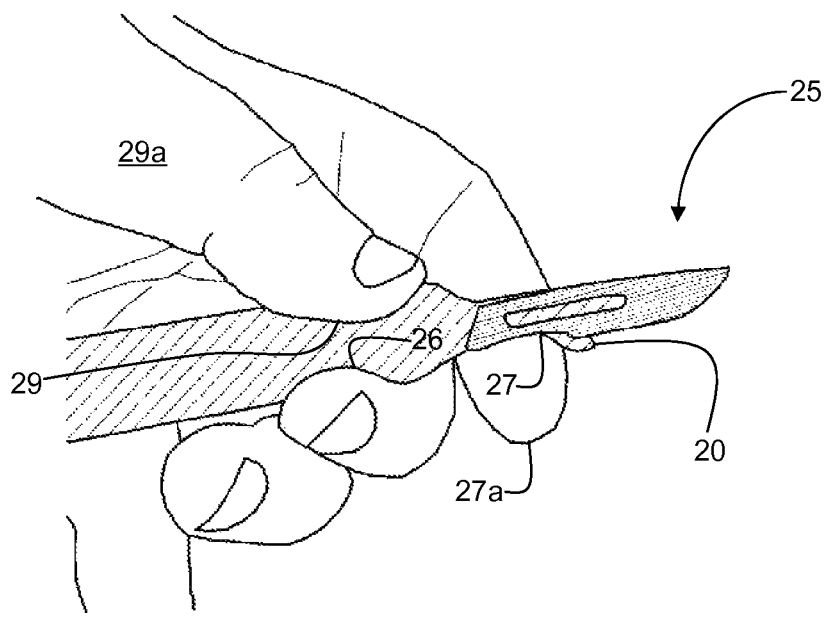

FIGS. 8 and 9a show further embodiments of a scalpel 25 having an elongated handle 10 whose distal end is of generally similar construction to that shown in FIG. 6 and described above. They are the same embodiment but used in reverse modes. However, in FIG. 8 opposite the first depression 26 for accommodating the user's thumb, thus allowing the handle to be gripped between the middle finger 26a and the thumb 29a, which are accommodated in the first depression 26 and the third depression 29, respectively. The user's index finger 27a is accommodated within the second depression 27 in a manner similar to the embodiment shown in FIG. 7. The first depression 26 and the third depression 29 serve to facilitate swiveling the handle 10 by gentle rotation of the middle finger and the thumb, thus allowing the blade 11 to be tilted sideways for insertion into the working surface at a non-normal angle. Such an arrangement is particularly suited to right-handed users.

Figure 10D:
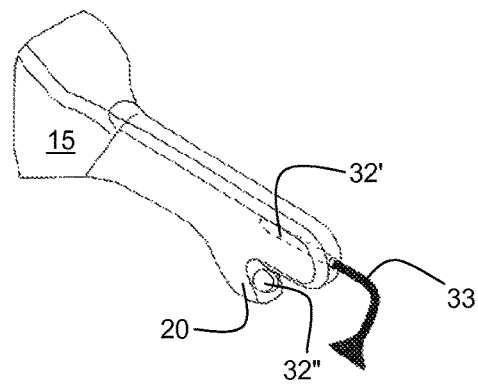
Figure 10E:
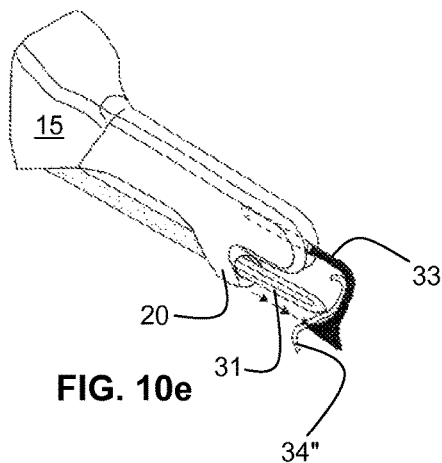
Figure 10F:
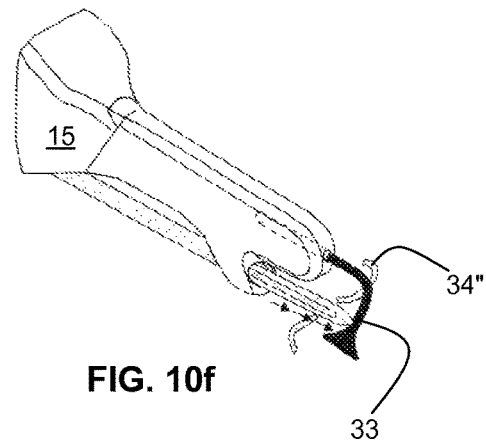
Figure 10G:
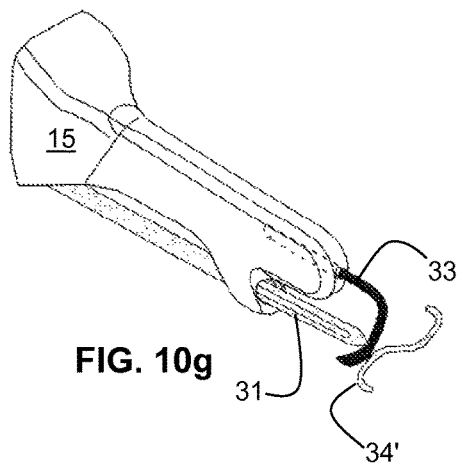
Figure 10H:
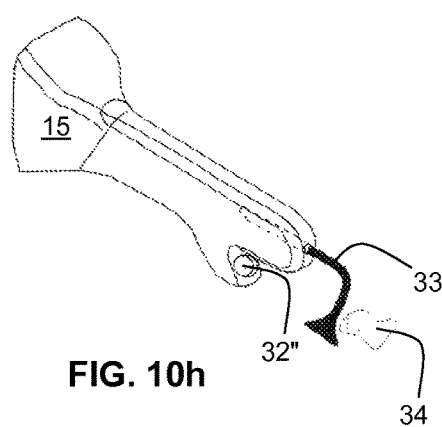

FIG. 9a shows the same embodiment as FIG. 8 when used in an opposite sense. FIGS. 7, 8 and 9a are all held in the left hand. FIG. 9b shows a variation where two projections 20 are symmetrically disposed on opposite sides of the scalpel so as to allow the scalpel to be held in either hand. FIG. 9c likewise shows a variation that may be held in either hand and where opposing projections 20 are formed very close to the working tip, thus allowing the tool to be brought very close to the workpiece. The embodiments in FIGS. 9b and 9c are typically held vertically such as when applied to dental tools that are introduced into and controlled from within the oral cavity. Although the working tip is shown as a blade 11, it will appreciated that other working tips may be provided, such as are shown by way of example in FIGS. 10a to 10c.

FIG. 10a shows pictorially an embodiment of an instrument a front end of whose handle 10 has a sufficiently wide cross-section to accommodate therein a support 30 for attaching an accessory tool 31. The support 30 may be a screw-threaded bore 32 formed in the handle or a recess adapted to frictionally engage the accessory. FIG. 10b shows an embodiment where the support 30 is provided through the body of the projection 20. By way of example, the accessory tool 31 is shown as a probe in FIG. 10a but it may equally well be an extraction tool having a hooked end as shown in FIG. 10b, FIG. 10c shows yet a further embodiment where supports 30 are provided in different parts of the mount 15, which by way of illustration is shown as a two-sided mount having opposing elongate protrusions 16a and 16b as shown in FIG. 6a. Although multiple supports are shown, in practice only one is required but the drawing is merely illustrative of several possible locations, although of course more than one support may be provided. Furthermore, it is to be noted that in all of the variations shown in FIG. 10c, there is no projection. Thus, FIG. 10c refers to a different aspect of the invention, which does not require a projection but still allows for an accessory to be attached to a finger-held instrument such as, but not limited to, a surgical scalpel.

FIGS. 10d to 10h show embodiments wherein bores 32' and 32" are formed in both the front surface of the mount 15 and also through the projection 20. The bore 32" passes completely through the projection 20 so as to allow a cutting tool 31 to be slidably accommodated therein and to be moved forward and backwards by the surgeon. Different types of shield 33 are accommodated in the bore 32'. Thus, in FIG. 10d, the shield is shaped to be looped over rearward tissue 34' (shown in FIG. 10g) that lies behind forward tissue 34" (shown in FIG. 10e) that needs to be severed during a surgical procedure, thus shielding the rearward tissue 34' from being accidentally cut or otherwise damaged.

FIG. 11 shows a modification to the mount 15, which has a narrow waist shaped for easy gripping between the user's thumb and index finger of the user's right or left hand, allowing the instrument to be manipulated in a manner that depends on the type of operation being performed.

FIG. 12 shows a manner of using the scalpel 25 shown in FIG. 7, where the user places his index finger against a side surface of the projection 20. This allows the user to locate his index finger very close to the tip of the blade 11, thus facilitating fine control while the projection 20 acts as a guard that prevents injury.

FIGS. 13a and 13b show an alternative manner of using the scalpel 25 of FIG. 7, where the user grips the mount between his thumb and index finger with the index finger on the upper inactive surface of the blade and the thumb within the recess abutting the projection 20. The scalpels in FIGS. 13a and 13b are mirror images of each other and while both are suitable for use by left- and right-handed users, they are used differently depending on whether the user is left- or right-handed. In both cases, the blade 11 is flush with a mating surface of the projection 20, such that the mating surface is uppermost and the projection 20 points downward relative to the paper. When the scalpels are held vertically with the blade pointing downward, the blade is located on the inside i.e. toward the left of a right-handed user and to the right of a left-handed user. In both cases, the reverse surface of the projection remote from the blade serves as a finger guard for protecting the user's index finger. Thus, referring to FIG. 13*a*, the tip of the blade 11 points from left to right and may be used by a left-handed user (as shown) whose thumb is saddled within the recess and partially engages the lower edge of the projection 20 and whose index finger may either engage the upper edge of the mount 15 in contact with the upper inactive edge of the blade 11 or may rest against the surface of the finger guard. The blade may thus be gripped between the thumb and index finger with the thumb ideally positioned behind the rear surface of the projection for providing fine control and with the index finger safely shielded by the finger guard. When the blade of the scalpel is held substantially vertical, the index finger of the left hand rests on the rear surface of the projection, which serves as a finger guard when performing a regular incision. Alternatively, the scalpel may be rotated so as to render the blade flush with the working surface, whereby the blade is positioned for slicing the working surface when pushed upward by the user's left thumb against the inactive edge of the blade. In this case, the finger guard is uppermost and supports the user's left index finger. However, the same tool rotated through 180° in the plane of the paper may be used by a right-handed user with the blade flush with the working surface, whereby the blade is positioned for slicing the working surface when pulled downward by the user's index finger. In both cases, the finger guard is uppermost relative to the plane of the working surface and supports the user's left or right index finger.

FIG. 13*b* shows the opposite construction suitable for regular incisions by a right-handed user who would hold the scalpel 25 in the same manner. In this case, a right-handed user would hold the scalpel in his right hand with the blade flush with the working surface for slicing the surface using a pushing motion. The same tool could be held by a left-handed user with the blade flush with the working surface for slicing the surface using a pulling motion. Here also, in both cases, the finger guard is uppermost relative to the plane of the working surface and supports the user's left or right index finger.

In either case, the projection 20 allows the user to locate his thumb and index finger very close to the tip of the blade 11, thus facilitating fine control while the projection 20 acts as a finger guard that prevents injury. During regular use with the blade 11 oriented vertically for performing incisions, left- and right-handed users will usually prefer to work with the respective tool. However, either tool may be used by both left- and right-handed users in a horizontal orientation for shaving the working surface: the only difference being the direction in which the blade is moved i.e. pulled or pushed relative to the plane of the working surface. Furthermore, when used with blades having two opposed cutting edges on one blade, the same tool can be used with the blade flush against the working surface to shave the working surface using both a pulling and pushing motion. Alternatively, the same effect can be achieved using a scalpel of the kind shown in FIG. 6*a* where two blades may be mounted on opposite sides of the mount with their cutting edges oriented in the same direction.

Use of the scalpel shown in FIGS. 13*a* and 13*b* is facilitated by virtue of the continuous plane surface of the finger guard which supports and shields the user's index finger without in any way impeding movement of the finger along its surface. This is distinct from known scalpels, whose handles have a textured or ridged surface that does not facilitate adjustment of the finger during use since the ridges engage the fleshy part of the finger and require momentarily releasing the grip in order to relocate the finger along the handle.

Figure 14:
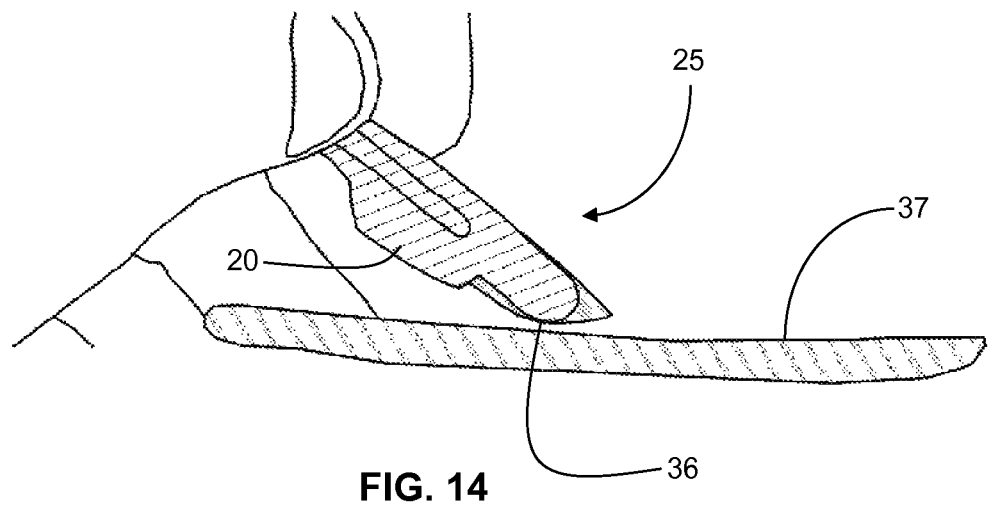
Figure 15:
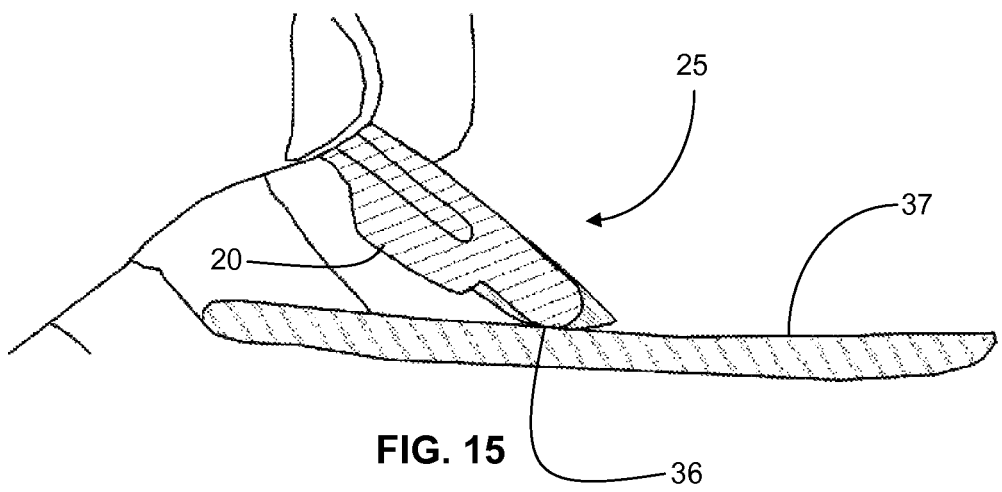

FIGS. 14 and 15 show a further embodiment of the scalpel 25 wherein the mount 15 is dimensioned so that a partial edge 36 thereof is tangential to a partial edge of the blade, thus preventing the partial edge of the blade from cutting a working surface 37. In one use of the scalpel, the scalpel 25 is placed on the working surface 37 in contact with the partial edge 36 of the mount 15 and is tilted forward as shown in FIG. 15 in order to cut the working surface with a proximal portion of the blade only. In an alternative use, the blade may be tilted about a horizontal axis using the partial edge of the mount as a fulcrum. The projection 20 serves as a depth gauge that ensures that the depth of cut remains substantially constant while also allowing the blade to enter the working surface with a longitudinal axis of the blade parallel to the working surface while being inclined at an angle to the longitudinal axis so that the planar surface of the blade severs the flesh at an oblique angle. This property has an added benefit when cutting skin since the internal opposing edges of the cut then have a larger surface that improves the healing process.

The projection may also be placed against a straight edge that serves as a track (not shown) thus allowing the surface of projection that is flush with the blade to ride against the track with the projection acting as a guide that ensures the blade follows the track. The opposite surface of the projection may serve as an abutment for slightly displacing internal body parts away from the edge of the blade so as to prevent inadvertent damage to the internal body parts.

Furthermore, when cutting the working surface 37 with the rear portion of the blade 11, the projection 20 rides along the working surface 37 helping to maintain it taut in the immediate proximity to the blade.

The surgical scalpel 25 shown in any of the figures may be used for therapeutic or diagnostic procedures, by:
- holding the handle near the blade between the thumb and middle finger,
- using the index finger to apply downward pressure to the working tip so as to
- cut into a patient's skin, and
- maintaining the projection in sliding contact with the patient's skin.

The projection 20 may be stretched across the patient's skin during forward movement of the scalpel so as to keep the skin taut and may be used as a fulcrum for tilting the scalpel about the projection when cutting into the patient's skin.

Figure 16:
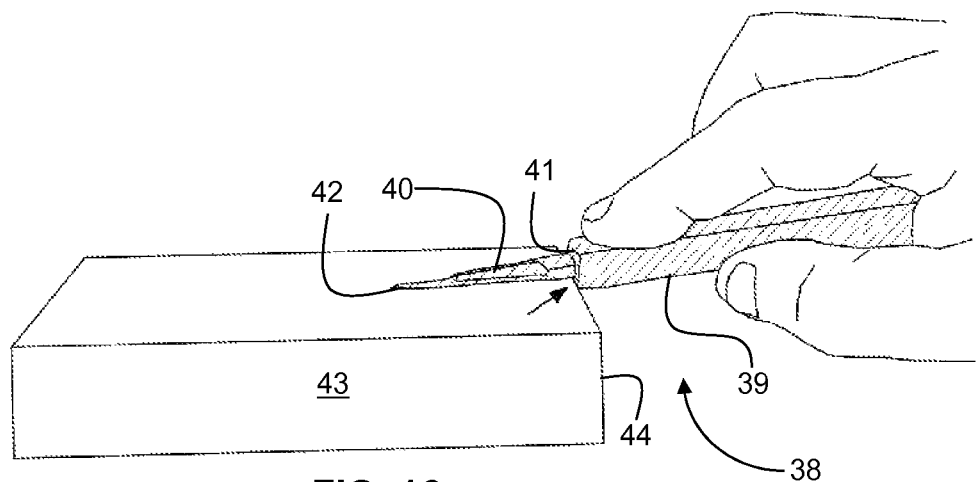
FIG. 16 is a pictorial representation showing a first limitation in the use of a common prior art surgical scalpel.

FIG. 16 is a pictorial representation showing a common prior art surgical scalpel 38 of the kind disclosed in FIG. 1 of US 2010/0324577 wherein a body portion 39 has a tang 40 that projects from an end face 41 thereof. A blade 42 of the scalpel is attached to the tang 40 is known manner. A limitation of such a construction is that when the scalpel 38 is drawn along a working surface 43 having an edge 44, the end face 41 creates a discontinuous surface between the body portion 39 and the tang 40, which is prone to catch the edge 44 thus limiting free movement of the scalpel.

US 2010/0324577 (Dunn) shows other embodiments such as FIG. 10A having profiled mounts where this limitation is less apparent. However, the scalpel appears to have a bulbous tang that is not amenable to being held with the blade substantially flush against a working surface. The scalpel is therefore not easily used to shave a surface of the working surface or to perform other similar actions.

Figure 17:
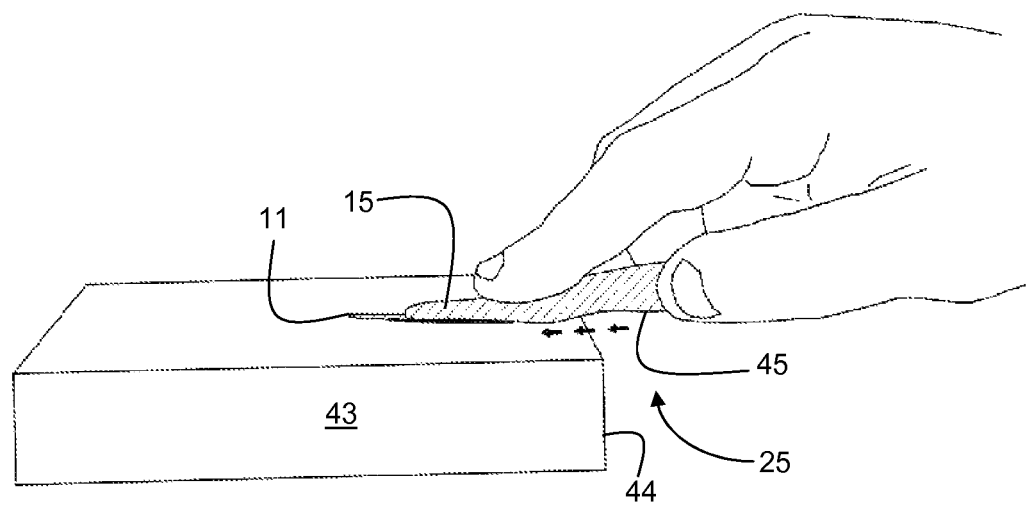
FIG. 17 is a pictorial representation showing how the surgical scalpel according to the invention overcomes the limitation shown in FIG. 16.

FIG. 17 shows pictorially how the surgical scalpel 25 according to the invention overcomes this limitation owing to the blade 11 being attached to a mount 15 that forms a continuous surface with a body portion 45 of the scalpel. Consequently, the handle has no discontinuity and may be edged across the working surface without impediment.

Figure 18:
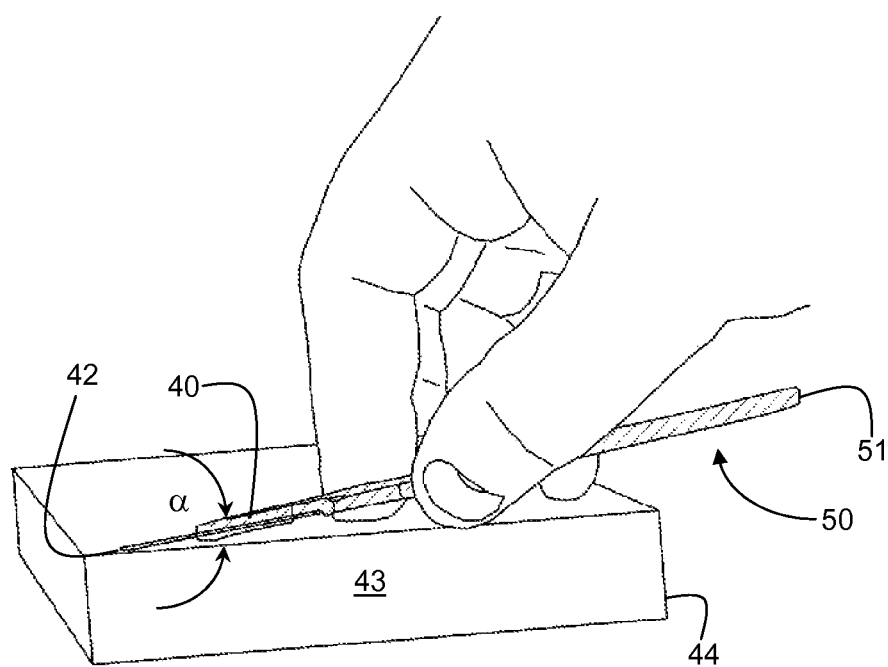
FIGS. 18 and 19 are pictorial representations showing further limitations in the use of a common prior art surgical scalpel.
Figure 19:
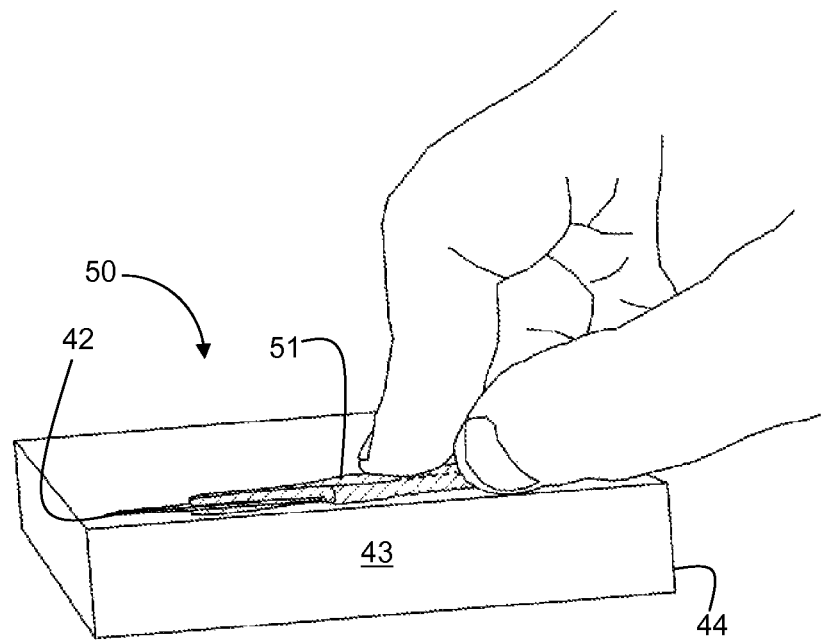

FIGS. 18 and 19 are pictorial representations showing another common prior art surgical scalpel 50 having a substantially planar body portion 51 to which a blade 42 is mounted via a tang 40. As can be seen in FIG. 18, the body portion 51 is typically gripped between the thumb and forefinger. FIG. 18 shows use of the scalpel to cut into a surface of the workpiece 43, while FIG. 19 shows use of the scalpel to shave a surface of the workpiece 43. In going from FIG. 18 to FIG. 19, the user gradually decreases the angle α subtended between the handle and the surface of the workpiece 43. Owing to the near planarity of the scalpel and its extremely narrow profile, it is seen that when the scalpel is used to shave the surface and is thus held substantially flat against the surface, it yields almost no surface that is amenable to being gripped. This forces the user to maneuver the scalpel into a position where it can be held from an end and interrupts the smooth flow of work that is essential to fine control particularly during surgical procedures.

Figure 20:
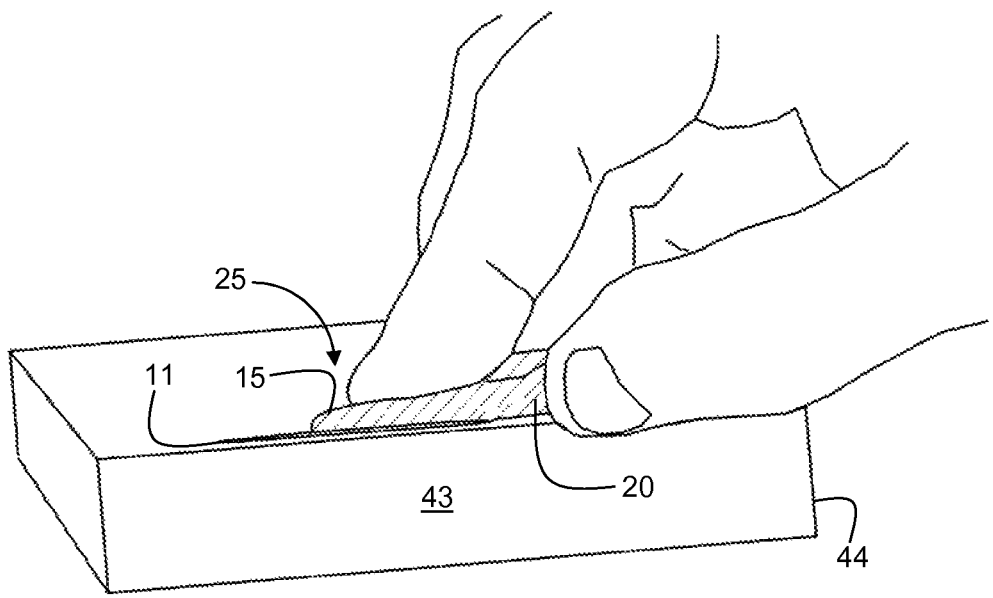
FIG. 20 is a pictorial representation showing how the surgical scalpel according to the invention overcomes the limitations shown in FIGS. 18 and 19.

FIG. 20 shows pictorially how the surgical scalpel 25 according to the invention overcomes these limitations owing to the increased profile offered by the projection 20 and the wider mount 15 allowing the handle to be gripped and maneuvered between thumb and forefinger even when the blade 11 is substantially flush with the surface.

Figure 21:
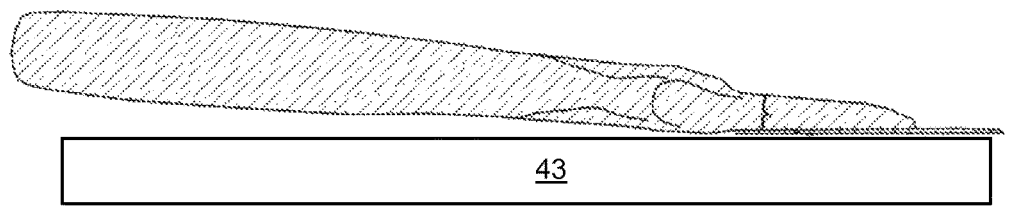
FIG. 21 shows further features of a surgical scalpel according to different embodiments of the invention.

FIG. 21 illustrates that the scalpel may be oriented at a slight acute angle to the working surface 43 with the blade resting flush on the working surface. The handle shown in the figure is profiled so that when the blade is flush with the working surface, the rear of the handle is upraised relative to the working surface thereby making it easier to get a grip on.

Figure 22A:
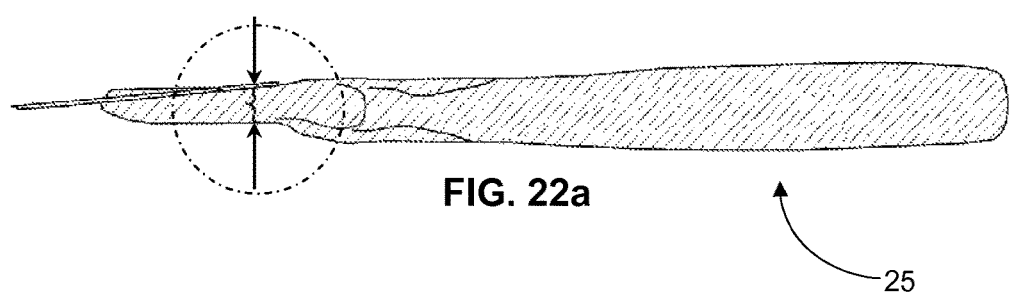
FIGS. 22a and 22b show further features of a surgical scalpel according to different embodiments of the invention.
Figure 22B:
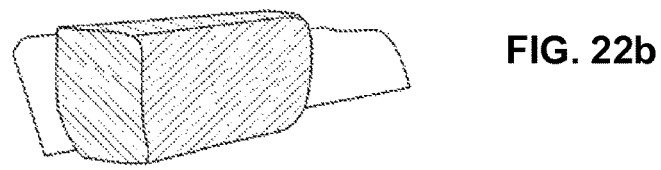
Figure 23A:
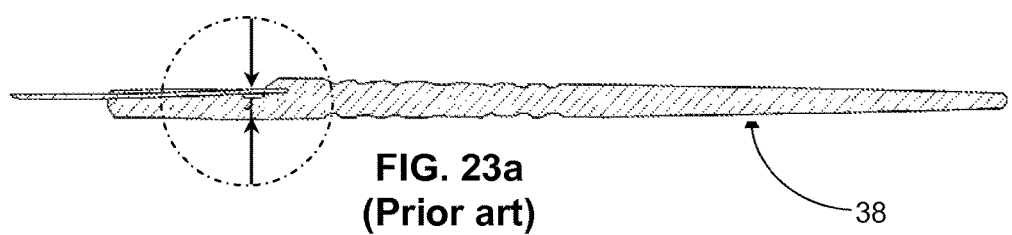
FIGS. 23a and 23b show comparable features of a prior art surgical scalpel.
Figure 23B:
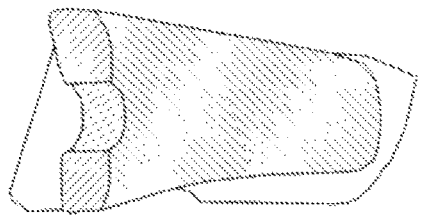

FIG. 22a is an elevation of the scalpel 25 according to the invention showing that it is significantly broader at the mount than conventional plastic scalpels shown as 38 in FIG. 23a. As a result, the scalpel according to the invention is much less susceptible to fracture. The cross-sections of the two scalpels through the respective points of the mount are shown in detail in FIGS. 22b and 23b, respectively. It will be seen that the scalpel shown in FIGS. 23a and 23b has a hole, which obviously significantly reduces the strength of the molding. However, while this is fairly common, not all prior art scalpels have such a hole but they are still more susceptible to fracture owing to their reduced cross-sectional area.

Figure 24:
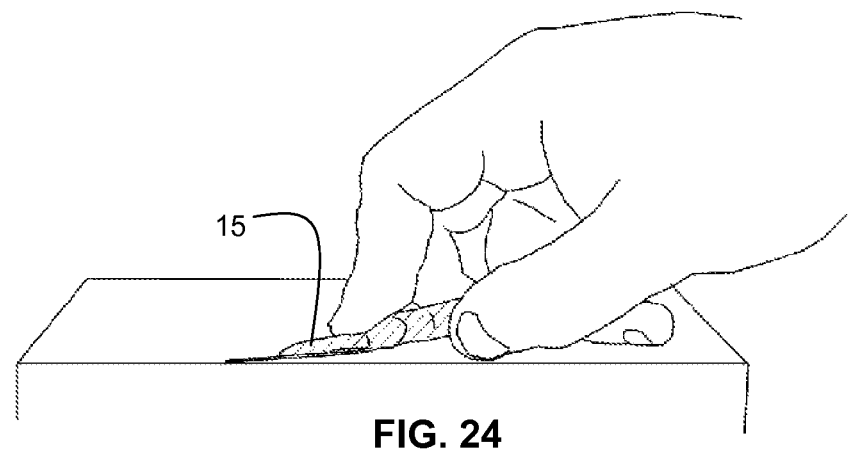
FIG. 24 shows further features of a surgical scalpel according to different embodiments of the invention.
Figure 25:
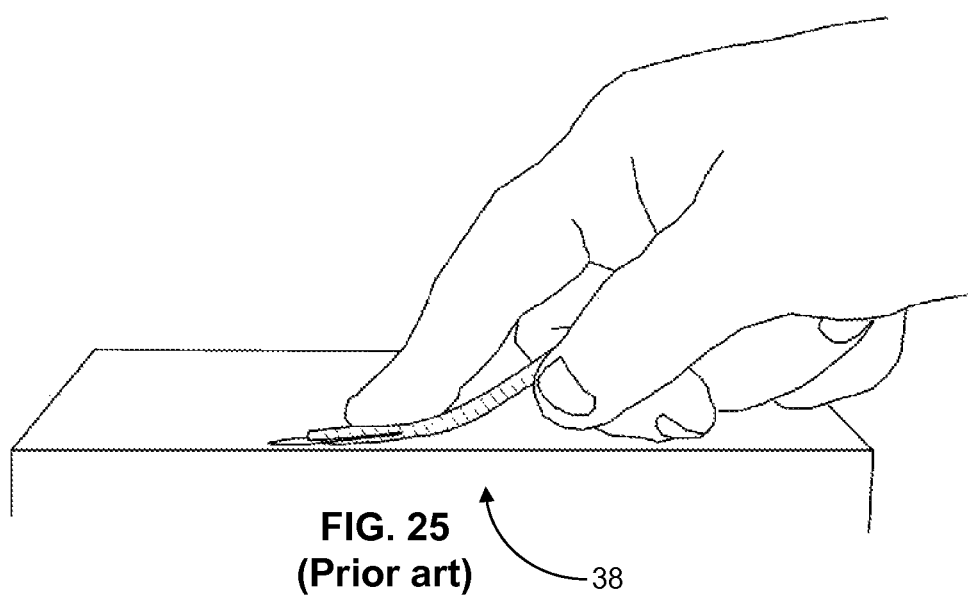
FIGS. 25 and 26 show comparable features of a prior art surgical scalpel.
Figure 26:
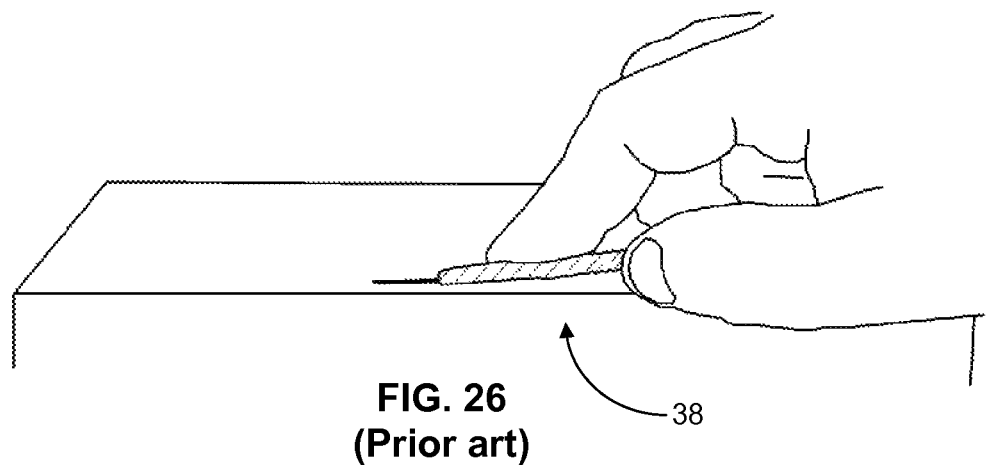

FIG. 24 shows use of the scalpel where downward pressure is applied by the user's index finger on the mount 15, thus subjecting the cross-section of the handle to internal stress. However, as noted above, owing to its greater cross-section, the handle withstands the stress without excessive bending or fracturing. As distinct from this, as shown in FIG. 25, albeit in exaggerated detail, the handle of a prior art scalpel 38 being formed of a plastic that is both less massive and less reinforced is prone to bend unlike scalpels having conventional metal handles as shown in FIG. 26, where pressure applied to the blade renders it susceptible to blade fracture close to its point of contact with the mount.

Figure 27A:
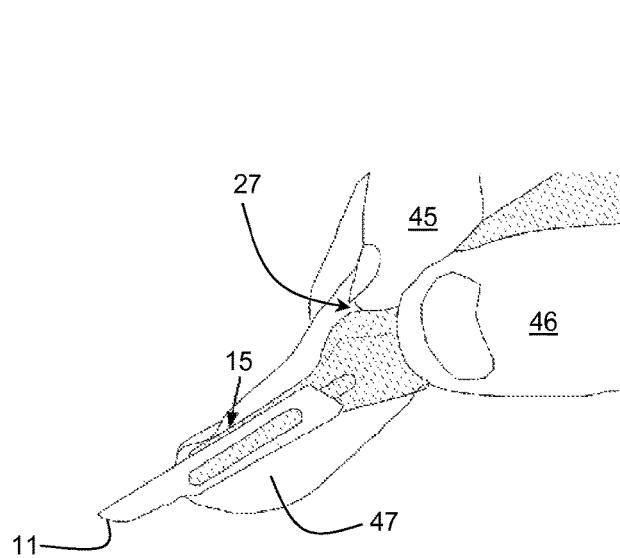
FIGS. 27a and 27b are pictorial representations showing the manner of gripping a surgical scalpel according to another embodiment of the invention.

FIG. 27a shows the shaped recess 27 in the upper surface of the handle that accommodates the user's index finger, as described previously with reference to FIG. 9. Consequently the user's index finger is recessed into the handle close to the blade rather than resting on its upper surface as is commonly the case in known scalpels where the finger tends to obscure the surgeon's line of sight such that he is unable to see the point of the scalpel while looking down the scalpel from its rear end. In the scalpel according to the invention this drawback is avoided and provides better visibility to the surgeon. Although the use of shaped handles for providing tactile feedback is known in the art, such as described in U.S. Pat. No. 7,150,754 col. 1, line 51, it has not been proposed to increase the visibility factor of a surgical scalpel by shaping the handle so that the surgeon's finger is recessed close to the blade in a shaped recess disposed in a known orientation relative to the blade while allowing the middle finger to hug the blade mount on the opposite side to the blade. Moreover, the index finger may be pressed against the working tip forward of the recess 27, while maintaining contact between the middle finger and the side of the mount. In both cases, the middle finger is shielded by the side surface of the mount allowing the scalpel to be safely gripped between the thumb and middle finger while the index finger may be used for fine control of the scalpel.

Figure 27B:
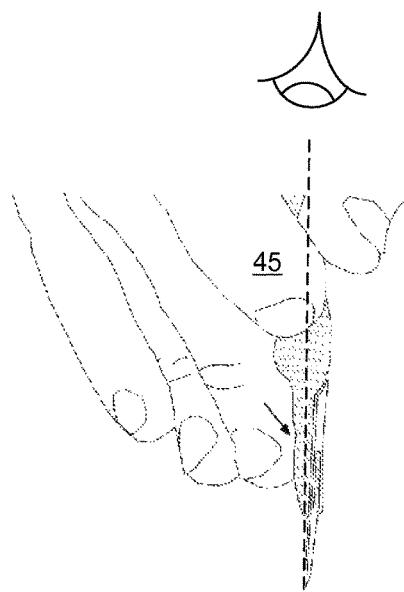
Figure 28A:
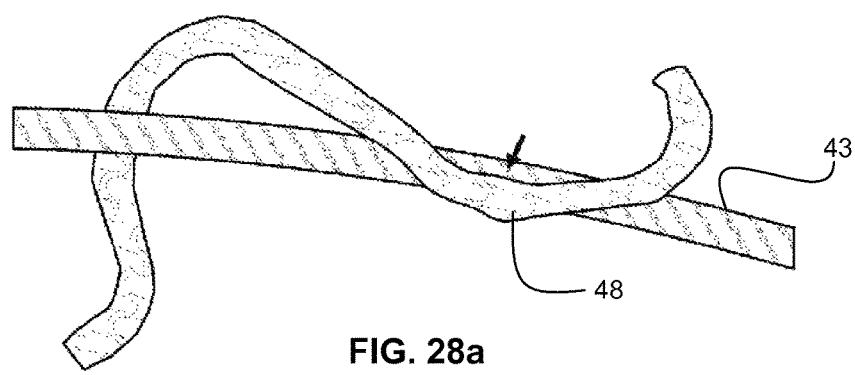

FIGS. 27a and 27b are pictorial representations taken from different vantage points showing the manner of gripping a surgical scalpel according to another embodiment. Thus, there is shown a detail of a scalpel having a blade 11 attached on one side of a mount 15. In use, the user grips the scalpel between index finger 45 and thumb 46 with the index finger 45 located within the recess as described above and the thumb 46 disposed against the side of the scalpel. The middle finger 47 lies flat against the rear side of the mount 15, i.e. that side to which the blade 11 is not attached, which thus shields the index finger while allowing it to control the scalpel during cutting. FIGS. 28a and 28b show a further benefit of the projection 20, which may be used to dislodge tissue 48 that overlaps and obscures the working surface 43 thus preventing inadvertent damage to the tissue 48 when cutting the working surface 43. Typically, the front edge of the projection 20 is used to engage the tissue 48, which is then moved aside so as to be well clear of the blade when cutting the working surface 43.

FIG. 29a shows a scalpel 25 according to another embodiment of the invention having a double-sided mount such as described above with reference to FIG. 6. On one side of the mount 15 there is attached a scalpel blade 11 while on the opposite side of the mount there is attached a tool guide or gauge 52 having a blunt edge, such as shown in FIG. 29b. The scalpel blade points downward into the working surface 43. The tool guide or gauge 52 is constructed similar to a regular scalpel blade such as described above with reference to FIGS. 2a and 2b and is keyed to an elongate protrusion on the mount 15 that is complementary to a slot 12 in the tool guide. Since the tool guide 52 and the blade 11 are attached to opposite sides of the mount 15, each via a respective elongate protrusion 16a and 16b as shown in FIG. 6, there is a gap between them corresponding to the width of the mount 15. In use, the blade 11 may be used to cut straight parallel to an edge against which the tool guide 52 is maintained in abutting relationship. By such means, so long as the tool guide 52 maintains contact with the straight edge, it is ensured that the blade 11 cuts straight. Likewise, the blunt lower edge of the tool guide 52 may serve as an arresting element, which prevents the blade 11 from penetrating deeper than the lower edge of the tool guide 52. In such configuration, the tool guide 52 functions a depth gauge since it sets a maximum depth of cut beneath which the blade 11 is prevented from exceeding. Additionally, since the tool guide 52 is forward of the working tip of the blade 11, it may serve to exert downward pressure on the working surface ahead of the blade and thus keep it taut without the need for an external accessory or another tool. The lower edge of the tool guide 52 may also serve to iron out kinks in the working surface and shift obstructions in the path of the blade.

FIG. 30*a* shows a mount 15 according to another embodiment, which may optionally be a double-sided mount, of which only one mounting surface is shown. The mount has an elongated protrusion 16 abutting a rear landing area 55 that supports the rear surface of a blade 11 as shown in FIG. 2*a* having a slanted rear edge. In order to provide rigid support for the blade, the rear landing area 55 supports a pair of upwardly projecting main ridges 56, 57 that have a complementary slant to the rear edge of the blade and thus serve as abutments for the rear edge of the blade, in order to facilitate removal of the blade, a channel 58 is formed in the mount that extends beyond the main ridges 56, 57 so as to be accessible from the rear edge of the blade. The blade is removed by inserting a lever into the channel and prying the blade off the rear landing. The main ridge 57 abuts an auxiliary landing area 59 that is thus slightly higher than the rear landing area 55 and which itself supports an auxiliary ridge 60, which is slanted in a direction opposite to that of the main ridges 56 and 57. The auxiliary ridge 60 is configured to abut the slanted rear edge of a blade 61 of opposite orientation as shown in 30*b*. By such means, the same mount is able to rigidly support blades having slanted rear edges of mutually opposed orientations.

FIGS. 31*a* and 31*c* show respectively elevations of the blades 11 and 61. FIG. 31*b* shows in elevation an alternative mount 15 similar to that shown and described in FIG. 30*a* but having a support shield 20, which is optional since the principles of the mount shown in FIG. 30*a* are clearly independent of whether or not the shield is provided.

FIG. 32*a* shows pictorially a prior art surgical scalpel 65 whose tang 67 is bent at a fixed angle to a planar handle 66 at a line 68 where the tang 67 joins the handle 66. Typically, such scalpels are made of stainless steel and are susceptible to bending either during manufacture or by the end-user using moderate force. The reason the end-user may wish to bend the scalpel in this manner is so that the handle is easier to manipulate when the blade 11 is substantially co-planar with the working surface 43. This is difficult when the blade and the handle are collinear as explained above with reference to FIG. 19. Prior to bending the blade 11 is flush with the tang 67 and with lower portion of the handle 66. However, when the scalpel is bent, the blade remains flush with the tang to which it is firmly attached, but the rear edge 69 of the blade, which overhangs the tang no longer lies in the plane of the handle.

FIG. 32*b* shows pictorially a surgical scalpel 25 according to the invention whose handle 10 is formed of a material that allows it to be bent at a desired angle at a line 68 where it meets the tang 15 and to maintain its shape under load. The line 68 lies beyond the rear edge of the blade 11 and so, in this case, bending the handle preserves full contact between the blade and the whole of the tang. The facility to bend the tool while retaining the full area of the rear portion of the blade within the ambit of the tang is due to a combination of geometry and material. The prior art scalpel shown in FIG. 32*a* cannot do this partly because it is typically made of stainless steel that can only be bent by heating. Thus, it cannot be done by the end-user, or at least not easily. But even in the factory where this is not a problem, there is insufficient bulk of material rear of the tang to support the rear portion of the blade once the tang is bent.

The handle and tang of the surgical scalpel 25 shown in FIG. 32*b* are normally formed of high grade plastics, typically but not necessarily polycarbonate. The cross-section of the tang where it meets the rear portion of the blade is sufficiently narrow to allow bending without the need for heating. But the geometry ensures that the tang still has sufficient bulk and area behind the rear portion of the blade to fully overlap the rear portion of the blade after bending.

Figure 33A:
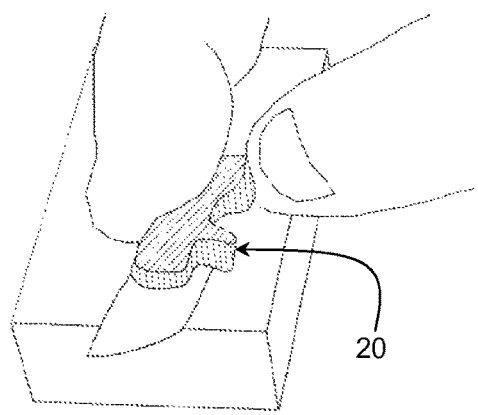
FIGS. 33a to 33f show pictorially surgical scalpels having shaped shield portions according to different embodiments.

FIGS. 33*a* to 33*f* show pictorially surgical scalpels having shaped shield portions according to different embodiments. FIG. 33*a* shows a scalpel having a projection 20 that depends from a mount 15 whose side surfaces are planar thus allowing the scalpel to rest flat on a workpiece. The workpiece is cut by slight tilting of the scalpel relative to the workpiece so as to bring the blade into contact with the workpiece.

Figure 33B:
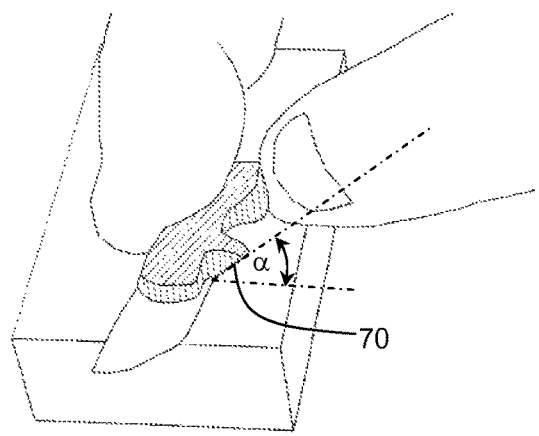

FIG. 33*b* is a variation on the embodiment of FIG. 33*a* where an end surface 70 of the projection 20 is chamfered at an acute angle $\alpha$ so that the mount 15 is tilted by a defined angle. The chamfered end surface 70 of the projection 20 then rests on the workpiece so that the tool is held stably during cutting.

Figure 33C:
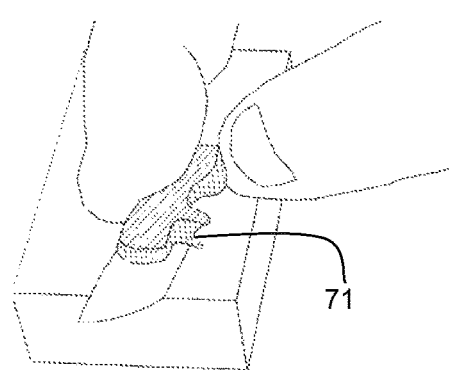
Figure 33D:
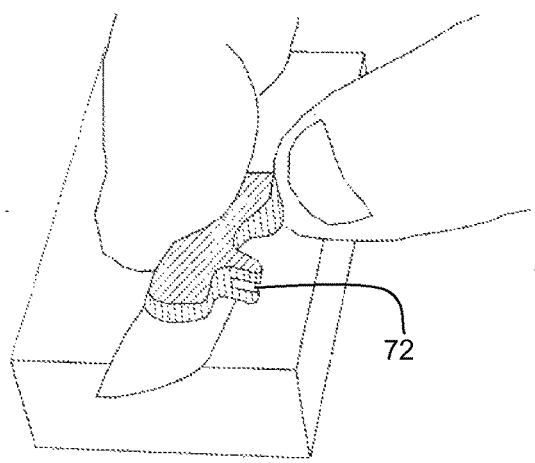

FIGS. 33*c* and 33*d* show variations of a further embodiment where the projection 20 has an arcuate groove 71 or a slot 72 parallel to the blade 20. In use, the groove or slot rides along a vertical projecting beveled or straight edge of a guide (not shown) thus allowing extremely fine and accurate control of the blade along a contour parallel to the edge of the guide.

Figure 33E:
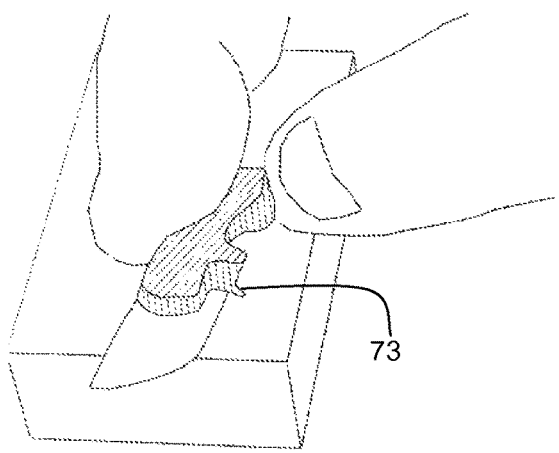

FIG. 33*e* shows a further variation, which is similar to that of FIGS. 33*c* and 33*d* except that instead of a slot having two opposing guide surfaces, the projection is in the form of a single guide surface 73 that is adapted to run along a vertical projecting edge of a guide (not shown).

Figure 33F:
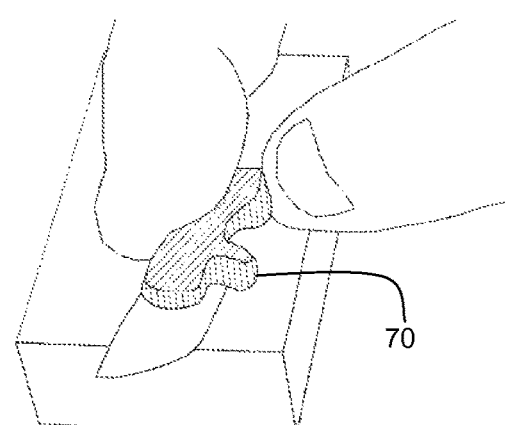

FIG. 33*f* has a projection 20 whose end surface 70 is beveled so as to allow the blade to be laterally tilted during use.

Although the invention has been described with particular reference to a surgical scalpel whose working tip is a blade, it will be appreciated that it may be any suitable finger-held instrument such as a pen, craft knife or other non-surgical knife, probe and so on.

The working tip may be supported on the handle by a retractable mechanism as known per se.

Although a large number of embodiments have been described and illustrated, it is to be understood that the specific features of different embodiments can be combined. Conversely, specific features may be used independently also in tools where the handle has no shield.

It should also be noted that in all embodiments the tool may be an electrically operated device coupled to a battery or other suitable electrical power supply via a wire or cable. Likewise, the invention contemplates finger-held electrical tools having a working tip mounted at the end of a handle, projecting from which a shield or projection is adapted for exerting a contact force on the working surface so as to shield the operator's finger from the working tip while allowing for fine control of the working tip during use. For example, the principles of the invention are applicable to cauterization devices, laser and other microsurgical tools, apex locators and other such instruments.

Likewise, the working tip need not be an active device but may be passive such as commonly used for diagnostic purposes. Such a tip may include an optical sensor or probe.

The invention also contemplates a double ended tool having a working tip at opposite ends of the handle as well as a tool having at least one rotatable tip.

The appended claims form an integral part of the disclosure and the wording of the claims is intended to complement the description, such that any embodiments defined by the claims using different language to that of the detailed description are to be construed as if they were described in the detailed description.

The invention claimed is:

1. A finger-held instrument comprising a handle, the handle including:
   a mount located at a distal end region of the handle;
   a projection supported by or on a portion that is part of the mount; and wherein
   the mount is a tang having a planar side surface supporting at least one elongate protrusion adapted for engaging a slot in a blade that has a planar surface whereby the blade may be mounted flat on the planar side surface of the tang, and wherein the mount extends along a longitudinal axis of the handle as to have a proximal end extending from a support portion of the handle and a distal, free end,
   the projection extends away from the mount in a direction orthogonal to the longitudinal axis and in a common direction with a plane extension of the planar side surface of the tang that is coplanar with the planar side surface such that the projection is configured to extend, relative to the common direction with the plane extension, out past a free edge of the blade when the blade is mounted on the tang,
   the handle further comprising a first depression shaped for accommodating a finger or thumb of the user, and which first depression is formed in the support portion of the handle as to be proximal to the proximal end of the mount, and
   the handle includes a second depression having a distal end that abuts a proximal edge of the projection, and which second depression is shaped for supporting a user's finger or thumb, and wherein said second depression and proximal edge of the projection are configured to serve as a finger or thumb reception area that presents an abutment that is shaped for both contact with an outer peripheral region of the user's finger or thumb and in a manner that allows contact pressure to be applied by the finger or thumb on the projection while precluding finger or thumb slippage past the projection and into contact with a sharp edge of the blade, and wherein the proximal edge is positioned, relative to the common direction with the plane extension, between an edge of the protrusion and an outermost, again relative to the common direction with the plane extension, edge of the projection.

2. The finger-held instrument according to claim 1, wherein the elongate protrusion projects from a side surface of the tang in a direction that is perpendicular to both a direction of extension of the projection away from the tang and the longitudinal axis of the handle.

3. The finger-held instrument according to claim 1, wherein the mount is dimensioned so that a partial edge thereof is tangential to a partial edge of the blade.

4. The finger-held instrument according to claim 1, further comprising a blade which is supported on the mount as to be removable from the handle.

5. The finger-held instrument according to claim 1, wherein the handle includes a finger push ridge and depression combination, with the ridge and depression combination being elongated in a common direction as the longitudinal axis of the handle on a surface of the mount that is opposite the planar side surface of the tang.

6. The finger-held instrument according to claim 1, which is configured to be a surgical scalpel instrument.

7. The finger-held instrument according to claim 1, further including a third depression formed in a side of the handle opposite the first depression for accommodating the user's finger or thumb, thus allowing the handle to be gripped between a finger and thumb, which are accommodated in the first depression and the third depression, respectively and allowing the handle to be swiveled by rotation of the middle finger and the thumb.

8. The finger-held instrument according to claim 1 having two opposing elongate protrusions on opposite sides of the tang each for supporting a respective blade.

9. The finger-held instrument according to claim 1, wherein the mount includes a collet that is configured for rotatably mounting the blade therein.

10. The finger-held instrument according to claim 1, wherein the mount is configured such that the blade is rotatably attached to the handle.

11. The finger-held instrument according to claim 1, wherein the mount includes at least one accessory support for attaching an accessory thereto.

12. The finger-held instrument according to claim 1, wherein the projection includes at least one accessory support that is provided through a body of the projection.

13. The finger-held instrument according to claim 11, wherein two or more accessory supports are provided in different parts of the mount.

14. The finger-held instrument according to claim 1, wherein the projection has a side surface that is coplanar with the plane extension of the planar side surface of the tang.

15. The finger-held instrument according to claim 1, further comprising a blade, and wherein the blade has two opposed cutting edges for shaving the working surface using both a pulling and pushing motion.

16. The finger-held instrument according to claim 1, having a pair of protrusions extending out to opposite sides of the tang and being adapted to support a pair of opposing blades having respective cutting edges pointing in the same direction for shaving the working surface using both a pulling and pushing motion with respective ones of said blades.

17. The finger-held instrument according to claim 1 being configured as a knife or scalpel instrument comprising:
   a double-sided mount having opposing elongate protrusions defining a gap therebetween corresponding to a width of the mount,
   a blade mounted on a first side of the mount and being adapted for pointing downward into a working surface, and
   a tool guide or gauge having a blunt edge mounted on an opposite side of the mount.

18. The finger held instrument according to claim 1, wherein the first and second depressions and the projection are on a common, underside of the handle when a sharp edge of the blade is positioned on the same underside of the handle.

19. The finger held instrument according to claim 18 further comprising a third depression that is in between the first and second depressions along the longitudinal axis of the handle and positioned on an upper side of the handle when the sharp edge of the blade is positioned on the underside of the handle.

20. A handle for supporting at an end thereof a blade, the blade being configured for cutting a working surface and having a slot, the handle comprising:
   a mount projecting from the end of the handle and having at least one elongate protrusion adapted for engaging the slot, the mount being elongated and extending along a longitudinal axis of extension of the handle and having a proximal end that is supported by a support portion of the handle and a distal, free end,
   a projection located on the mount between the distal and proximal ends of the mount, and the projection being configured as to extend out away from the mount along a direction perpendicular to the longitudinal axis of extension;
   a first depression positioned proximal to the projection and being formed in the support portion of the handle, said first depression being shaped for accommodating a finger or thumb of the user; and a second depression positioned distal to the first depression and proximal to the projection and having a distal depression section partially defining the second depression and extending to a proximal edge of the projection, and which second depression defines a concave cavity that has opposite longitudinally spaced proximal and distal ends that are spaced apart longitudinally wide enough to receive a full pad width of a user's finger or thumb, and wherein the mount and the end of the support portion of the handle to which the mount is attached form a continuous contoured surface which includes a raised surface that rises up and drops down in height at an interface region where the mount is attached to the support portion, and which raised surface has a proximal side that partially defines a third depression that accommodates a user's finger or thumb, and wherein the projection is further configured to have a base region that is integral with an edge region of the mount, and which base region has a distal end, in the longitudinal direction, that is proximal to a distal end of the protrusion.

21. The handle according to claim 20, wherein each elongate protrusion projects from a respective side surface of the mount in a direction that is perpendicular to both the direction of extension of the projection away from the mount and the longitudinal axis.

22. The handle according to claim 20, wherein:
   the at least one elongated protrusion abuts a rear landing area for supporting a rear surface of a blade having a slanted rear edge, said rear landing area supporting a pair of upwardly projecting main ridges that have a complementary slant to the rear edge of the blade and serve as abutments for the rear edge of the blade;
   one of the main ridges abuts an auxiliary landing area that is slightly higher than the rear landing area and which itself supports an auxiliary ridge that is slanted in a direction opposite to that of the main ridges; and
   the auxiliary ridge is configured to abut the slanted rear edge of a blade of opposite orientation;
   whereby the mount is able to rigidly support blades having slanted rear edges of mutually opposed orientations.

23. The handle according to claim 20, wherein:
   the mount and the projection have respective first and second bores for supporting respective accessories therein.

24. A finger-held instrument comprising a handle, the handle including:
   a mount located at a distal end region of the handle;
   a projection supported by the mount, and wherein
   the mount is a tang having a planar side surface supporting at least one elongate protrusion adapted for engaging a slot in a blade that has a planar surface whereby the blade may be mounted flat on the planar side surface of the tang, and wherein the mount extends along a longitudinal axis of the handle as to have a proximal end extending from a support portion of the handle and a distal, free end,
   the handle comprising first means for accommodating a finger or thumb of the user,
   the handle further comprising second means for accommodating a finger or thumb of the user, and wherein the projection is further configured to have a base region that is integral with an edge region of the mount, and which base region has a distal end, in the longitudinal direction, that is proximal to a distal end of the protrusion.

25. A finger-held instrument comprising:
   a handle, the handle having a mount located at a distal end region of the handle;
   a projection supported by or on a portion that is part of the mount;
   an accessory tool, and wherein
   the mount extends along a longitudinal axis of the handle as to have a proximal end extending from a support portion of the handle and a distal, free end,
   the projection extends away from the mount in a direction orthogonal to the longitudinal axis, and
   the handle comprising a first depression shaped for accommodating a user's finger or thumb, and a second depression shaped for accommodating a finger or thumb of the user,
   the first depression being positioned in the support portion of the handle, and the second depression being positioned on the mount such that the second depression is positioned distal to the first depression and proximal to the projection, the second depression having a distal depression section partially defining the second depression and extending to a proximal edge of the projection, and which second depression defines a concave cavity that has opposite proximal and distal ends that are spaced apart longitudinally wide enough to receive a full pad width of a user's finger,
   and wherein at least one of the projection and the mount have an accessory bore that is configured for reception of the accessory tool.

* * * * *